US010729157B2

(12) United States Patent
Hillman et al.

(10) Patent No.: US 10,729,157 B2
(45) Date of Patent: Aug. 4, 2020

(54) METHODS FOR REGULATING WEIGHT AND SIZE OF ANIMALS

(75) Inventors: Jeffrey Daniel Hillman, Gainesville, FL (US); Eric W. T. Chojnicki, Gainesville, FL (US); Ravi Shankar Orugunty, Alachua, FL (US)

(73) Assignee: Oragenics, Inc., Alachua, FL (US)

( * ) Notice: Subject to any disclaimer, the term of this patent is extended or adjusted under 35 U.S.C. 154(b) by 2487 days.

(21) Appl. No.: 11/265,414

(22) Filed: Nov. 2, 2005

(65) Prior Publication Data

US 2006/0093650 A1 May 4, 2006

Related U.S. Application Data

(60) Provisional application No. 60/624,228, filed on Nov. 2, 2004.

(51) Int. Cl.
| | | |
|---|---|---|
| *A23L 33/175* | (2016.01) | |
| *A61K 31/185* | (2006.01) | |
| *A23K 20/142* | (2016.01) | |
| *A61K 31/198* | (2006.01) | |
| *A23L 33/00* | (2016.01) | |
| *A23L 33/17* | (2016.01) | |

(52) U.S. Cl.
CPC ............ *A23K 20/142* (2016.05); *A23L 33/17* (2016.08); *A23L 33/175* (2016.08); *A23L 33/30* (2016.08); *A61K 31/185* (2013.01); *A61K 31/198* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,792,549 A | 12/1988 | Takahasi | |
| 5,312,985 A | 5/1994 | Dhaon et al. | |
| 5,484,623 A * | 1/1996 | McLean | 426/601 |
| 5,914,326 A * | 6/1999 | McCarty | A61K 31/205 |
| | | | 424/655 |
| 6,281,244 B1 | 8/2001 | Schneider et al. | |
| 2002/0136785 A1* | 9/2002 | Yuan | A61K 31/704 |
| | | | 424/728 |
| 2004/0235923 A1* | 11/2004 | Abe | A23L 2/52 |
| | | | 514/400 |

FOREIGN PATENT DOCUMENTS

| | | | |
|---|---|---|---|
| DE | 126104 | 6/1977 | |
| EP | 0882451 | 6/1998 | |
| WO | 98/04255 | 2/1998 | |
| WO | WO 02100193 A1 * | 12/2002 | A23L 2/52 |
| WO | 2006050432 | 5/2006 | |

OTHER PUBLICATIONS

Derwent abstract of DD 126104A, Original document published Jun. 22, 1977.*
McNamara et al., Journal of Neuroscience, 10(12), p. 3970-3976, 1990.*
Kelley et al., JBC 187(2), p. 529-535, 1950.*
Sullivan et al., Public Health Reports, 47(2), p. 75-83, 1932.*
Swenseid et al. J Nutr 80(1), 99-102, 1963.*
Markweise et al. Alcohol Clin Exp Res, 22(2), p. 416-421, 1998, abstract only.*
Kalman et al. Nutrition 15(5) p. 337-340, 1999.*
Zinke et al. Development 126 p. 5275-5284, 1999.*
Waziri, "Glycine Therapy of Schizophrenia: Some Caveats", Society of Biological Physchiartry, 1996:39:155-156.
Waziri, "Glycine Therapy of Schizophrenia", Biol. Physchiatry, 1996;40:p. 684-686.
Javitt, "Glycine modulators in schizophrenia", Investigational Drugs, vol. 3, No. 7, p. 1067-1072, 2002.
Shoham, et al., "Chronic High-Dose Glycine Nutrition: Effects on Rat Brain Cell Morphology", Society of Biological Psychiatry, 2001;49:876-885.
Javitt, "Management of Negative Symptoms of Schizophrenia", Curr. Physchiatry Reports, vol. 3, No. 5, p. 413-417, 2001.
Shoham, et al., "High dose glycine nutrition affects glial cell morphology in rat hippocampus and cerebellum", Internatinal Journal of Neurophychopharmacology, (1999), 2, 35-40.
Shoham, et al. "Glycine and D-cycloserine attenuate vacuous chewing movements in a rat model of tardive dyskinesia", Brain Research, 1004 (2004) 142-147.
Tuominen, et al., "Glutamatergic drugs for schizopheria: a systematic review and meta-analysis", Schizophrenia Research 72 (2005) 225-234.
Petzke, et al., "Utilization of [1-14C] Carbon of Glycine of High Glycine Diet Fed Young and Old Rats", Z. Alternsforsch. 42/6 (1987) 323-328.
Aust, et al., "The hypolipaemic action of a glycine rich diet in rats", Di Nahrung, 24, 7, 1980, 663-671.
Sugiyama, et al., "Dietary Sulfur-Containing Amino Acids and Glycine as Determinant Factors in Plasma Cholesterol Regulation in Growing Rats", J. Nutr. Sci. Vitaminol., 31, 121-125, 1985.
Park, et al., "Dietary Taurine or Glycine Supplementation Reduces Plasma and Liver Cholesterol and Triglyceride Concentrations in Rats Fed a Cholesterol-Free Diet", Nutrition Research, vol. 19, No. 12, pp. 1777-1789, 1999.
Yoshida, et al., "Effects of Addition of Arginine, Cystine, and Glycine to the Bovine Milk-Simulated Amino Acid Mixture on the Level of Plasma and Liver Cholesterol in Rats", J. Nutr. Sci. Vitaminol., 34, 567-576, 1988.
Olsen, et al., "Effect of Amino Acid Diets upon Serum Lipids in Man" The American Journal of Clinical Nutrition vol. 23, No. 12, 1970, pp. 1614-1625.
Yagasaki, et al., "Effects of Dietary Methionine, Cystine, and Glycine on Endogenous Hypercholesterolemia in Hepatoma-Bearing Rats", J. Nutr. Sci. Vitaminol., 32, 643-651, 1986.
Jusko, et al., "Corticosteriod Pharmacodynamics: Models for a Broad Array of Receptor-Mediated Pharmacologic Effects", J. Clin. Pharmacol., 1990;30:303-310.

(Continued)

*Primary Examiner* — Nissa M Westerberg
(74) *Attorney, Agent, or Firm* — DLA Piper LLP

(57) ABSTRACT

The invention provides methods and compositions for regulating weight and size in animals.

13 Claims, 20 Drawing Sheets

(56) References Cited

OTHER PUBLICATIONS

Dayneka, et al, "Comparison of Four Basic Models of Indirect Pharmacodynamic Responses", Journal of Pharmacokinetics and Biopharmaceutics, vol. 21, No. 4, p. 457-478, 1993.
Thompson, et al., "Putting the Rap on Akt", Journal of Clinical Oncology, 22:4217-4226, 2004.
Heatwole, "TUNEL Assay for Apoptotic Cells", Methods in Molecular Biology, vol. 115, p. 141-148, 1999.
Gaillard, et al., "Growth of Preadipocyte Cell lines and Cell Strains from Rodents in Serum-Free Hormone-Supplemented Medium", In Vitro, vol. 20, No. 2, p. 79-88, 1984.
Senthilkumar, et al., "Glycine Modulates Hepatic Lipid Accumulation in Alcohol-Induced Liver Injury", Pol. J. Pharmacol., 2003, 55, 603-611.
Ratnayake, et al., "Influence of dietary protein and fat on serum lipids and metabolism of essential fatty acids in rats" British Journal of Nutrition, (1997) 78, 459-467.
Castagne, et al., "An animal model with relevance to schizophrenia: sex-dependent cognitive deficits in osteogenic disorder-shionogi rats induced by glutathione synthesis and dopamine uptake inhibition during development", Neuroscience, 123 (2004) 821-834.
Williams, et al, "Effects of typical and atypical antipsychotics on human glycine transporters", Schizophrenia Research, 71 (2004) 103-112.
El Hafidi, et al., "Glycine intake decreases plasma free fatty acides, adipose cell size, and blood pressure in sucrose-fed rats", Am. J. Physiol. Regul. Interg. Comp Physiol. 287: R1387-R1393, 2004.
Yagasaki, et al, "Effects of Dietary Methionine and Glycine on Serum Lipoprotein Profiles and Fecal Sterol Excretion in Normal and Hepatoma-Bearing Rats", J. Nutr. Sci. Vitaminol., 36, 45-56, 1990.
Alvarado-Vasquez, et al., "Effect of glycine in streptozotocin-induced diabetic rats", Comparation Biochemistry and Physiology Part C, 134 (2003) 521-527.
Batta, et al, "Effect of Hydrophobicity of Bile Acids and Their Conjugation with Glycine and Taurine on Apoptosis and Growth Arrest in Colon Cells", Hepatology, Vo. 32, No. 4, Pt. 2, 2000, 1342.
Beynen, et al., "Dietary glycine and cholesterol metabolism in rats" Z. Ernahrungswiss 26:161-164 (1987).
Budd, et al., "Signaling Events in NMDA Receptor-Induced Apoptosis in Cerebrocortical Cultures", Ann NY Acad. Sci, 893:261-4 (1999).
Fujita, et al., "Differential Expressions of Glycine Transporter 1 and Three Glutamate Transporter mRNA in th Hippocampus of Gerbils with Transient Forebrain Ischemia", Journal of Cerebral Blood Flow and Metabolism, 19:604-615, 1999.
Herrmann, "Effect of Taurine, Glycine and B-Sitosterols on Serum and Tissue Cholesterol in the Rat and Rabbit", Circulatin Research, vol. VII, p. 224-227, 1959.
Hirth, "Discovery of TNF-a Induced Apoptosis Inhibitors with Activity in a Murine Model of Multiple Sclerosis: Glycine Diamides", Abstracts of Papers of American Chemical Society. 2002, 224.
Jacob et al., "Glycine prevents the induction of apoptosis attributed to mesenteric ischemia/reperfusion injury in rat model", Surgery, vol. 134, No. 3, p. 457-466, 2003.
Leite, et al., "In vitro interaction of the glycine receptor with the leptin receptor", Physiology & Behavior, 77 (2002) 565-569.
Nyberg, et al., "Cytoprotective influence of ZVAD-fmk and glycine on gel-entrapped rat hepatocytes in a bioartifical liver", Surgery, vol. 127, No. 4, p. 447-455, 2000.
O'Donnell, et al., "Effects of 1.5% Glycine Infusion on the Nonelectrolyte Components of Serum in Dogs", The Prostate, 8:393-400 (1986).
Reichelt, et al., "The colon mitosis inhibitor Pyroglutamyl-histidyl-glycine inhibits growth of non-tumorgenic colonic epithelial cells", Anticancer Research 24:587-592 (2004).
Sakagami, et al., "Amino Acid Utilization During Cell Growth and Apoptosis Induction", Anticancer Research, 18:4303-4306 (1998).

Sugiyama, et al., "Amino acid composition of dietary proteins affects plasma cholesterol concentration through alteration of hepatic phospholipid metabolism in rats fed in a cholesterol-free diet", J. Nutritional Biochemistry, 7:40-48, 1996.
Zhang, et al., "Glycine Prevents Apoptosis of Rat Sinusoidal Endothelial Cells Caused by Deprivation of Vascular Endothelial Growth Factor", Hepatology, vol. 32, No. 3, p. 542-546 (2000).
Zhang, et al., "Glycine Prevents Apoptosis of Sinusoidal Endothelial Cells due to Vascular Endothelial Growth Factors (VEGF) Deprivation", Hepatology, 30(4):225A-225A, n. 259 (1999).
Muramatsu, et al., "Effect of Excess Levels of Individual Amino Acids on Growth of Rats Fed Casein Diets", J. Nutrition, 101:1117-1123 (1971).
Takeuchi, et al., "Effects of Ornithine and Some Amino Acids on the Growth Depression by Excess Glycine in Young Rats", Agr. Biol. Chem., vol. 35, No. 8, p. 1298-1303 (1971).
Takeuchi, et al., "Effects of Arginine and Methionine on the Growth Depression of Rats Fed Diets High in Glycine", Agr. Biol. Chem., vol. 33, No. 8, p. 1161-1168 (1969).
Takeuchi, et al., "Metabolim of L-Leucine-U-14C in Young Rats Fed Excess Glycine Diets", Agr. Bio. Chem., 39 (12), 2417-2419 (1975).
Miner, "The adipocyte as an endocrine cell", J. Anim. Sci. 2004, 82:935-947.
Houseknecht, et al., "The Biology of Leptin: A Review", J. Anim. Sci. 1998, 76:1405-1420.
Mantzoros, "The Role of Leptin in Human Obesity and Disease: A Review of Current Evidence", Ann Intern Med. 1999;130:671-680.
Emi, et al., "Missense Mutation (Gly—Glu 188) of Human Lipoprotein Lipase Imparting Functional Deficiency", The Journal of Biological Chemistry, vol. 265, No. 10, pp. 5910-5916 (1990).
Masters, et al., 14-3-3 Inhibits Bad-Induced Cell Death through Interaction with Serine-136:, Molecular Pharmacology, vol. 60, No. 6, 1325-1331 (2001).
Sandoval, et al., "Effect of Glycine on Hemoglobin Glycation in Diabetic Patients", Proc. West. Pharmacol. Soc. 42:31-32 (1999).
Cascio, "Structure and Function of the Glycine Receptor and Related Nicotinicoid Receptors", JBC Papers in Press, Manuscript published Mar. 15, 2004.
Rupnick, et al., "Adipose tissue mass can be regulated through the vasculature", PNAS, vol. 99, No. 16, 10730-10735 (2002).
Rose, et al., "Dietary glycine inhibits the growth of B16 melanoma tumors in mice", Carcinogenesis, vol. 20, No. 5, pp. 793-798 (1999).
Kolonin, et al., "Reversal of obesity by targeted ablation of adipose tissue", Nature Medicine, p. 1-8, 2004.
Ruggeri, et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models", Cancer Research, 63, 5978-5991 (2003).
Petzke, et al., "The effect of orally administered Glycine on metabolism", Die Nahrung Nutrition, 31 (1987) 3, 207-215 (German and English).
Frayn, et al., "Integrative physiology of human adipose tissue", International Journal of Obesity, (2003), 27, 875-888.
Guerre-Millo, "Adipose tissue hormones", J. Endocrinol. Invest. 25:855-861, 2002.
Kishida, et al., "Disturbed secretion of mutant adiponectin associated with the metabolic syndrome", Biochemical and Biophysical Research Communications, 306 (2003) 286-292.
Rabin, et al., "Adiponectin: linking the metabolic syndrome to its cardiovascular consequences", Expert Rev. Cardiovasc. Ther. 3(3), 465-471 (2005).
International Search Report for corresponding PCT/US2005/039657 dated Apr. 3, 2006.
Virdee, et al., "Phosphorylation of the pro-apoptotic protein BAD on serine 155, a novel site, contributes to cell survival", Current Biology, vol. 10, No. 18, p. 1151-1154 (2000).
Waziri, et al., "Glycine Therapy of Schizophrenia", Biol. Psychiatry, 1988;23:210-211.
Heresco-Levy, et al., "Efficacy of High-Dose Glycine in the Treatment of Enduring Negative Symptoms of Schizophrenia", Arch Gen Psychiarty, 56:29 (1999).

(56) References Cited

OTHER PUBLICATIONS

Olsson, et al., "Glycine toxicity after high-dose i.v. infusion of 1.5% glycine in the mouse", British Journal of Anaesthesia, 82 (2):250-4 (1999).
Amin, et al., "Dietary Glycine Inhibits Angiogenesis During Wound Healing and Tumor Growth", Cancer Biology & Therapy 2:2, 173-178 (2003).
Yamashina, et al., "Endothelial Cells Contain a Glycine-Gated Chloride Channel", Nutrition and Cancer, 40(2), 197-204 (2001).
Herbst, "Treatments for Painful and Other Fatty Lumps (Lipomatosis)", www.lipomadoc.org, Dec. 24, 2008.
Dalal et al., "Diagnosis and Management of Lipomatous Tumors", Journal of Surgical Oncology, vol. 97, pp. 298-313 (2008).
Rotunda et al., "Lipomas treated with subcutaneous deoxycholate injections", Journal of the American Academy of Dermatology, vol. 53, No. 6, pp. 973-978 (2005).
Bechara et al., "Lipolysis of Lipomas in Patients with Familial Multiple Liopomatosis: An Ultrasonography-Controlled Trial", Journal of Cutaneous Medicine and Surgery, vol. 10, No. 4, pp. 155-159 (2006).
Muller et al., "Zur Biochemie der benignen-symmetrischen Lipomatose (Adenolipomatose Launois-Bensaude, Madelung'sch Krankheit) = Biochemistry of benign-symmetrical lipomatosis (adenolipomatosis Launois-Bensaude, Madelung's disease)", Wiener Klinische Wochenschrift, vol. 88, No. 3, p. 94-101, (1976).
International Search Report dated Jul. 14, 2010, for corresponding application No. PCT/US10/024562.
International Search Report dated Aug. 23, 2011, for corresponding application No. PCT/US10/024562.
McNamara, et al., "Dual Effect of Glycine on NMDA-Induced Neurotoxicity in Rat Cortical Cultures", The Journal of Neurosicence, 10(12):3970-3976 (1990).

\* cited by examiner

Figure 1. Effect of Glycine Diet Treatment on Male Fisher Rats

Fig. 11A Phosphorylation of BAD in White Adipose Tissue from Sprague-Dawley Rats Treated with a High Glycine Diet
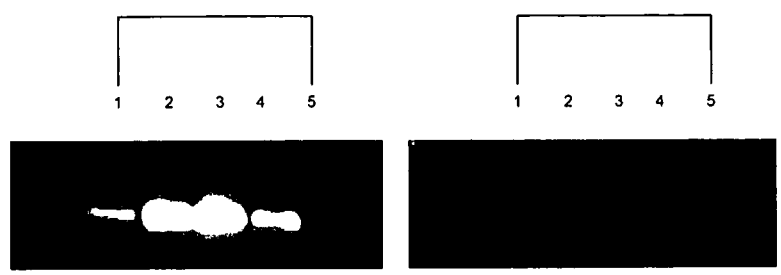
Fig. 11B Phosphorylation of BAD in Brown Adipose Tissue from Sprague Dawley Rats Treated with a High Glycine Diet
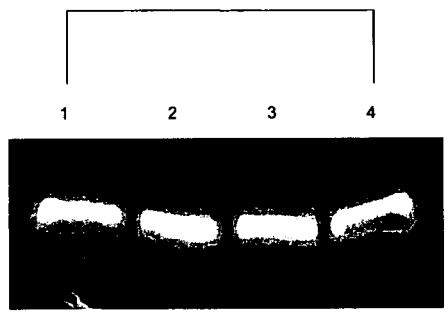

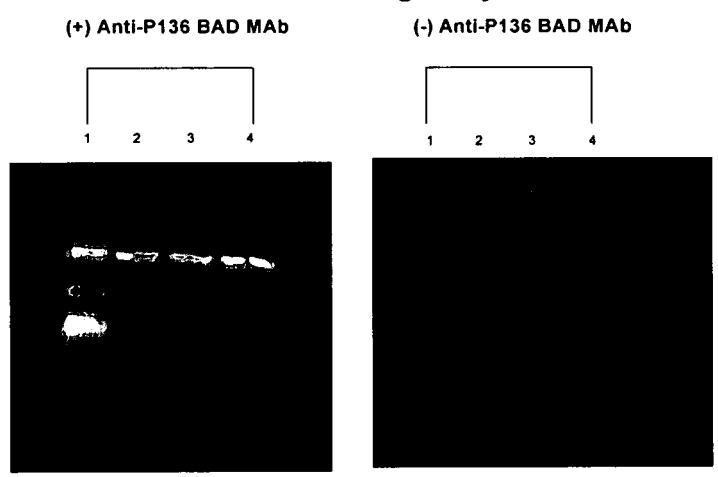
Figure 12. Phosphorylation of BAD in Liver Tissue from Sprague-Dawley Rats Treated with a High Glycine Diet

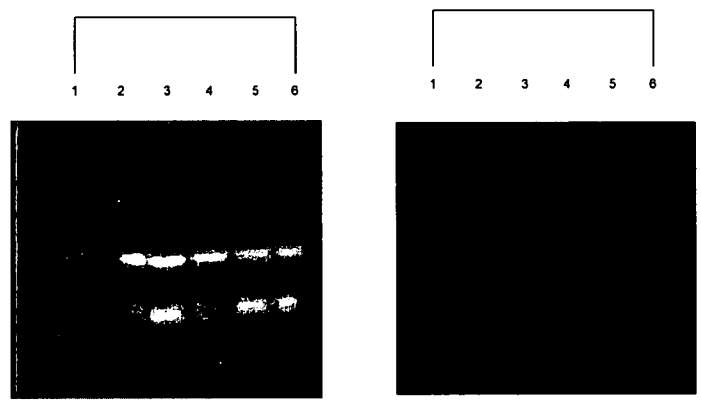
Figure 13. Phosphorylation of BAD in Muscle Tissue from Sprague-Dawley Rats Treated with a High Glycine Diet

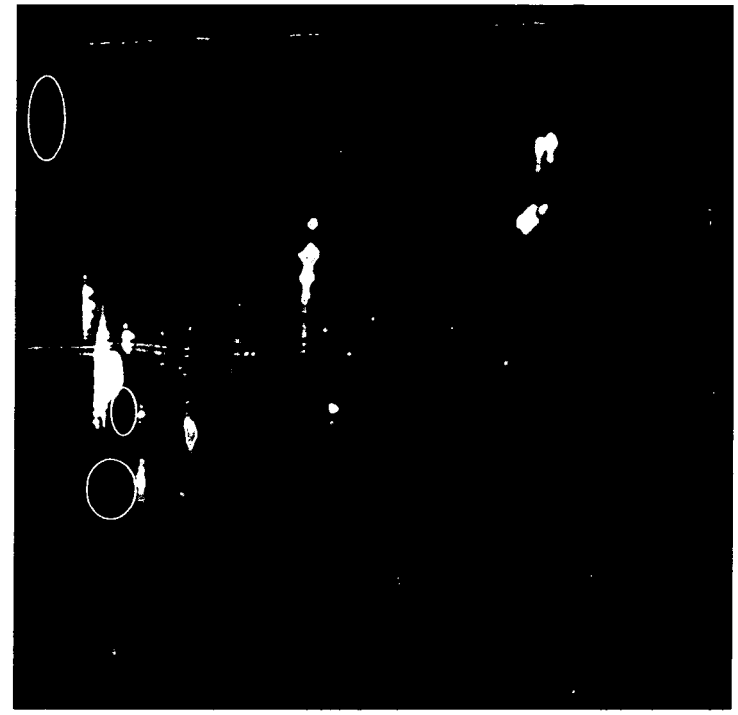
Figure 15: 20% Glycine Diet
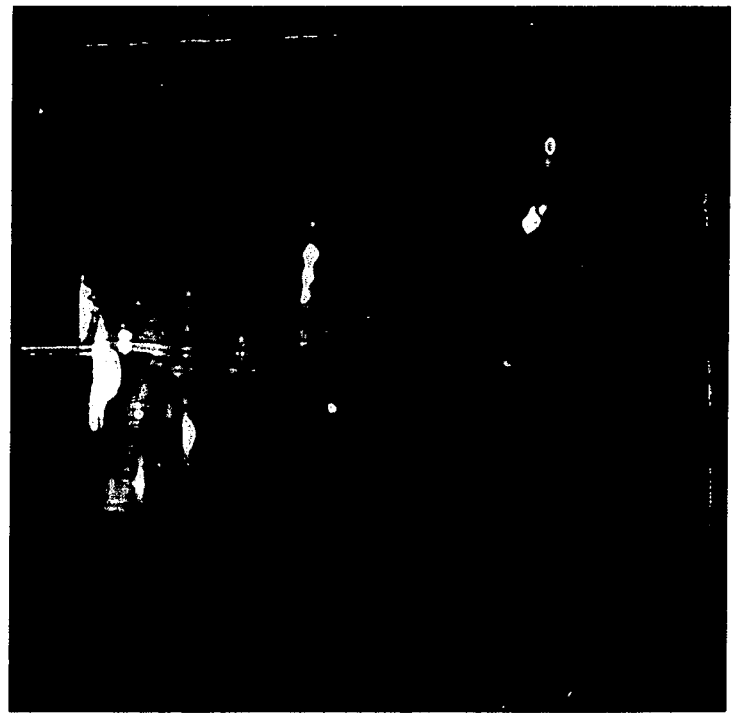
Figure 14: Control

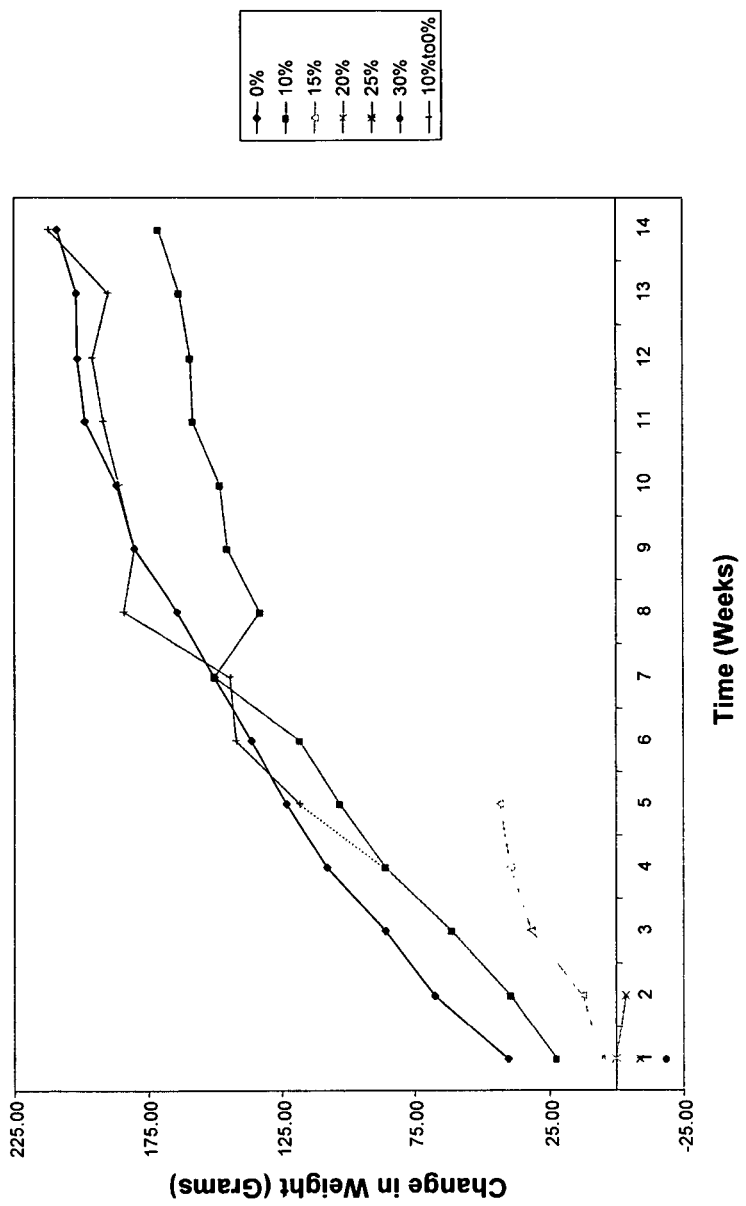
Figure 18. Dose Response of Immature Female Rat Weight to Glycine

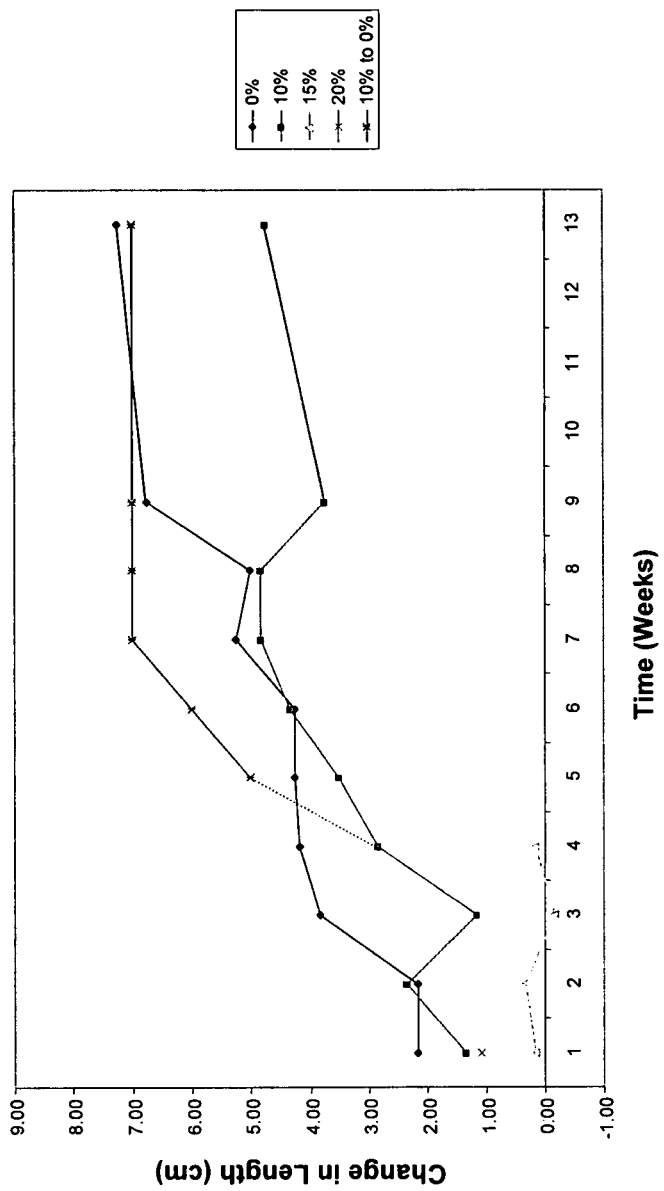

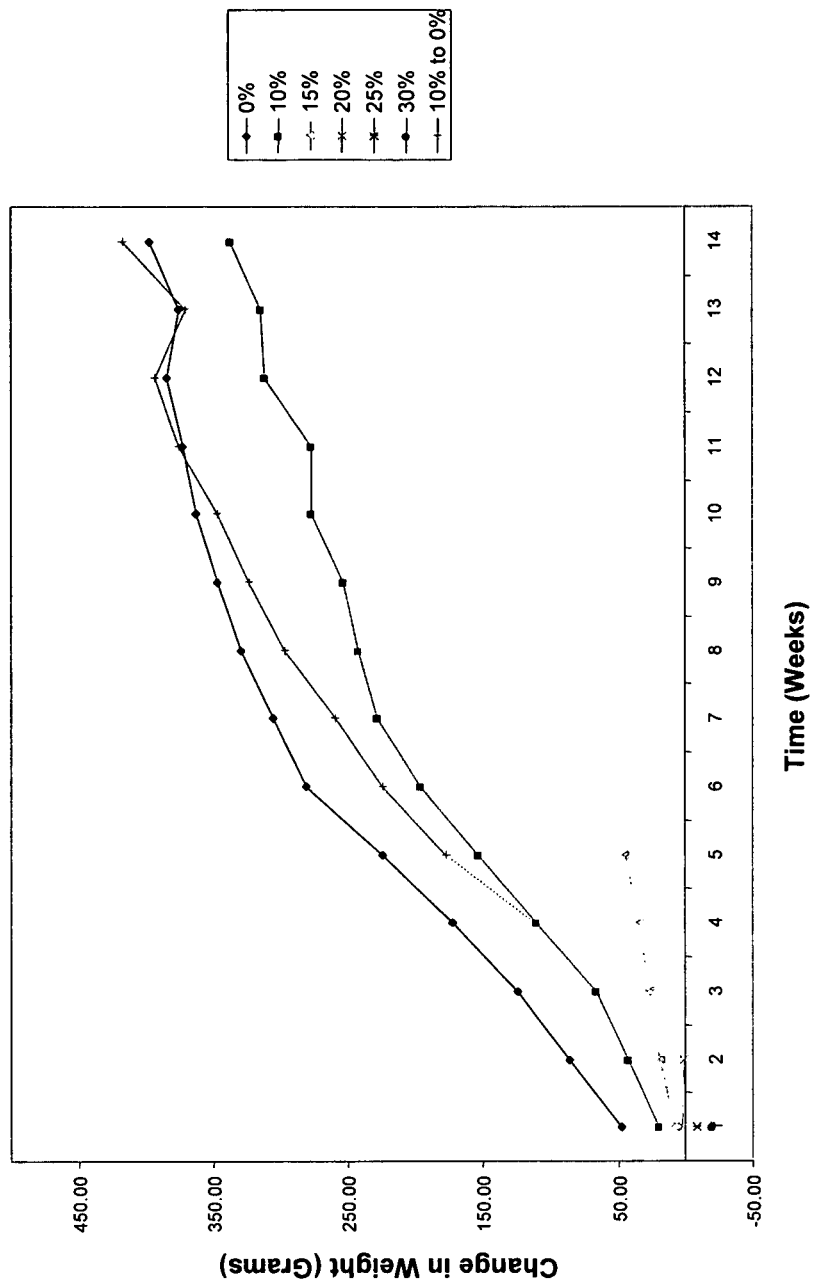
Figure 20. Dose Response of Immature Male Rat Weight to Glycine

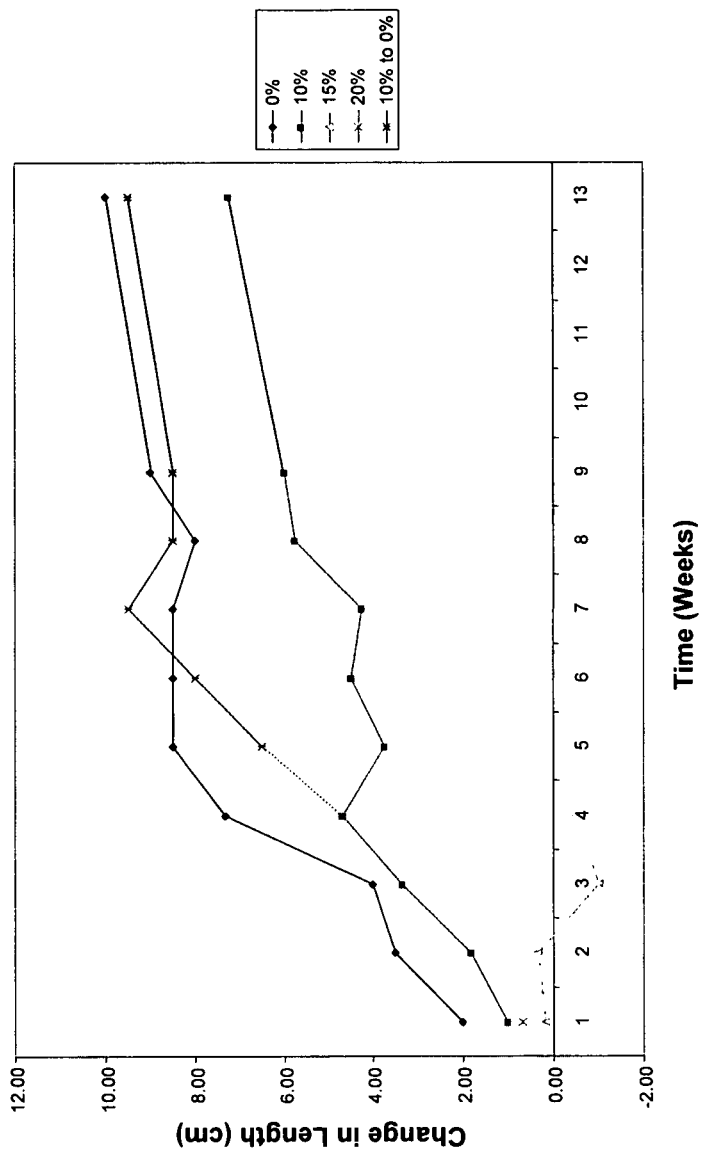

METHODS FOR REGULATING WEIGHT AND SIZE OF ANIMALS

PRIORITY

This application claims the benefit of U.S. Ser. No. 60/624,228, filed Nov. 2, 2004, which is incorporated herein in by reference in its entirety.

BACKGROUND OF THE INVENTION

In the United States it is estimated that 60% of adults meet the clinical requirements to be considered overweight or clinically obese resulting in 300,000 deaths annually. See, Eberhardt et al., *Urban and rural health chartbook.* 2001, Health, United States Hyattsville (MD): NCHS. p. 296; General, *The Surgeon General's call to action to prevent and decrease overweight and obesity:*2001, R.M. U.S. Department Health and Human Services, Editor. 2001. In 2001, the Surgeon General of the United States issued a call to action to prevent and decrease the incidence and prevalence of individuals that are overweight or clinically obese. *The Surgeon General's call to action to prevent and decrease overweight and obesity:*2001, R.M. U.S. Department Health and Human Services, Editor. 2001. Interestingly, in this report there is no mention of the application or use of a pharmaceutical approach to the problem. However, there is a great deal of interest in the development of a pharmaceutical approach by both industrial and academic research institutions. The pharmaceutical approach is attractive since there is a strong likelihood of greater compliance due to the probable ease of application and use.

Epidemiological studies from around the world have demonstrated an incontrovertible correlation between mortality and obesity. The progress that has been made over the past 50 years in achieving our health goals with regard to prevention and control of infectious diseases, heart disease, diabetes and certain cancers has been largely wiped out by the growing epidemic of obesity. In 2001, approximately 25% of children and teenagers were overweight, over twice the percentage from just 20 years ago. Currently, well over 60% of adults are found to be overweight or obese, and over 300,000 deaths per year can be directly attributed to these conditions in the U.S. alone. These findings cut across all races, ages, ethnic groups and both genders, although certain groups, particularly minority and low socioeconomic groups, are clearly more prone than others. *The Surgeon General's call to action to prevent and decrease overweight and obesity:*2001, R.M. U.S. Department Health and Human Services, Editor. 2001.

Overweight, defined as a body mass index (BMI ranging from 25-29.9 $kg/m^2$) and obesity (BMI>30 $kg/m^2$), has been correlated with premature death, type 2 diabetes, heart disease, stroke, hypertension, gallbladder disease, osteoarthritis, sleep apnea, asthma, various breathing problems, certain cancers, high blood cholesterol, pregnancy complications, increased surgical risk, psychological disorders, and other pathological conditions too numerous to list. *The Surgeon General's call to action to prevent and decrease overweight and obesity:*2001, R.M. U.S. Department Health and Human Services, Editor. 2001; NHLBI, *Clinical guidelines on the identification, evaluation, and treatment of overweight and obesity in adults,* N. NIH, Editor. 1998, HHS, PHS. p. 29-41. Obese individuals have a 50-100% increased risk of premature death from all these causes compared to persons with a BMI in the normal range (20-25 $kg/m^2$). Even modest weight loss (5-15% of excess total body weight) reduces the risk factors for a least some of these diseases, particularly heart disease, in the short term. NHLBI, *Clinical guidelines on the identification, evaluation, and treatment of overweight and obesity in adults,* N. NIH, Editor. 1998, HHS, PHS. p. 29-41. Current evidence suggests that the effect may have long-term benefits as well. See id.; NIDDK, *Study of health outcomes of weight-loss (SHOW) trial,* NIDDK, Editor. 2001, National Institutes of Health, U.S.A.

The Surgeon General's 2001 call to action to prevent and decrease overweight and obesity emphasizes the obvious changes in the American lifestyle during the past several decades, with an ever-increasing reliance on sources of poor nutrition and an increased sedentary lifestyle. His principal call to action is to promote education in the schools and throughout the community to encourage healthy eating and regular, adequate exercise. At this point in the ongoing process, it seems very likely that the vast majority of U.S. citizens have at least a cursory knowledge of this important message. However, the current trend toward obesity shows no signs of abating, and, in fact, is predicted to worsen over time. Clearly, the main obstacle to overcome is the need for compliance with regard to diet and exercise according to directed guidelines by the general population, which represents a dim prospect.

It is an interesting feature of the Surgeon General's 2001 report that essentially no mention is made of pharmaceutical approaches to the prevention and cure of overweight and obesity. Obviously, this is a keen area of interest among both academic and industrial institutions, since such an approach potentially could reduce the need for patient compliance. Enormous progress has been made in recent years in understanding the roles and functions of adipose tissue (reviewed by Frayn et al., *Integrative physiology of human adipose tissue.* Int J Obes Relat Metab Disord, 2003. 27(8): p. 875-88), both from the standpoints of regulation of energy storage and as a secretory cell. The picture that has emerged is very complex, since it involves the activity of the autonomic nervous system, the delivery of complex mixtures of substrates and hormones, feedback from autocrine and paracrine effectors secreted by adipocytes and also vascular supply to the fat tissue. Also, factors such as leptin and adiponectin secreted by adipocytes have a general effect on general metabolism. See, Guerre-Millo, *Adipose tissue hormones.* J Endocrinol Invest, 2002. 25(10):855-61; Kishida, *Disturbed secretion of mutant adiponectin associated with the metabolic syndrome.* Biochem Biophys Res Commun, 2003. 306(1):286-92; Miner, *The adipocyte as an endocrine cell.* J Anim Sci, 2004. 82(3):935-41; Rabin, et al., *Adiponectin: linking the metabolic syndrome to its cardiovascular consequences.* Expert Rev Cardiovasc Ther, 2005. 3(3):465-71; Houseknecht et al., *The biology of leptin: a review.* J Anim Sci, 1998. 76(5):1405-20; Mantzoros, *The role of leptin in human obesity and disease: a review of current evidence.* Ann Intern Med, 1999. 130(8):671-80.

From this, it is clear that a very integrative, holistic approach is required to gain a full understanding of the normal and pathological states that form the basis for the current problem with overweight and obesity described above.

Many types of animals are used for research, agriculture and companionship. In some instances the costs of housing and feeding such animals is great. Smaller-sized animals would cost less to feed and house than normal sized animals. Therefore, compositions and methods of producing reduced-sized animal(s) and/or reduced weight animal(s) can be advantageous. Also, obesity in companion animals is a problem. Obesity can cause shortened lifespan and many of the same diseases and conditions mentioned above for humans.

BRIEF SUMMARY OF THE INVENTION

In one embodiment the invention provides a method for inducing apoptosis in adipose tissue of an animal comprising administering a high glycine diet comprising about 10 to about 30% glycine to the animal. A high glycine diet can comprise glycine, glycine analogs, or a combination of glycine and glycine analogs.

Another embodiment of the invention provides a method for reducing adipose tissue in an animal comprising administering a high glycine diet comprising about 10 to about 30% glycine to the animal.

Still another embodiment of the invention provides a method for reducing phosphorylation of BAD at amino acid position 136 in adipose tissue of an animal comprising administering a high glycine diet comprising about 10 to about 30% glycine to the animal.

Yet another embodiment of the invention provides a method of reducing adipose cell size in an animal comprising administering a high glycine diet comprising about 10 to about 30% glycine to the animal.

Even another embodiment of the invention provides a method of reducing abdominal fat content in an animal comprising administering a high glycine diet comprising about 10 to about 30% glycine to the animal.

Another embodiment of the invention provides a method for producing weight loss in an animal comprising administering a high glycine diet comprising about 10 to about 30% glycine to the animal. The method can further comprise an adjunctive weight loss therapy such as an exercise regimen, a low-fat diet, a low-calorie diet, a low-carbohydrate diet, surgical intervention, behavioral therapy, pharmacotherapy, or a combination thereof.

Still another embodiment of the invention provides a method for producing a reduced-sized or reduced-weight animal and then returning it to a normal size. The method comprises administering a high glycine diet to an immature animal to produce a reduced-sized or reduced-weight animal and then administering a normal diet to the animal to produce a normal-sized or normal-weight animal.

Yet another embodiment of the invention provides a method for producing a reduced-sized or reduced-weight animal comprising administering a high glycine diet to an immature animal to produce a reduced-sized or reduced weight animal.

Even another embodiment of the invention provides a diet composition for weight reduction in an animal comprising about 10% to about 30% glycine, glycine analogs or combinations thereof and about 70% to about 90% of a low-calorie diet.

Another embodiment of the invention provides a diet composition for weight reduction in an animal comprising about 10% to about 30% glycine, glycine analogs or combinations thereof, and about 70% to about 90% of a low-fat diet. The low-fat diet can be a low-saturated fat diet.

Yet another embodiment of the invention provides a diet composition for weight reduction in an animal comprising about 10% to about 30% glycine, glycine analogs or combinations thereof and about 70% to about 90% of a low-carbohydrate diet.

Another embodiment of the invention provides a method for producing a reduced-size or reduced-weight or both reduced-sized and reduced-weight animal comprising administering a high glycine diet comprising about 10 to about 30% glycine to an immature animal.

Still another embodiment of the invention provides a method of inducing apoptosis in a white adipocyte, in vivo or in vitro, comprising administering one or more glycine analogs or a combination of glycine and glycine analogs to the adipocyte.

Even another embodiment of the invention provides a method of reducing phosphorylation of BAD at amino acid position 136 in a white adipocyte, in vivo or in vitro, comprising administering a one or more glycine analogs or a combination of glycine and glycine analogs to the adipocyte.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 11A-B shows the phosphorylation of BAD at tyrosine 136 in white adipose tissue and brown adipose tissue. FIG. 11 A: Lane 1: Molecular Weight Marker; Lane 2: Akt-phosphorylated BAD as positive control; Lane 3: Phosphorylated BAD from control rat; Lane 4: Phosphorylated BAD from rats fed 5% glycine diet; Lane 5: Phosphorylated BAD from rats fed 20% glycine diet). FIG. 11B: Lane 1: Akt-phosphorylated BAD as positive control; Lane 2: Phosphorylated BAD from control rats; Lane 3: Phosphorylated BAD from rat fed 5% glycine diet; Lane 4: Phosphorylated BAD from rats fed 20% glycine diet).

FIG. 12 shows the phosphorylation of BAD in liver tissue from Sprague-Dawley rats treated with a high glycine diet. Lane 1: Akt-phosphorylated BAD as positive control; Lane 2: Phosphorylated BAD from control rat; Lane 3: Phosphorylated BAD from rats fed 5% glycine diet; Lane 4: Phosphorylated BAD from rats fed 15% glycine diet.

FIG. 13 shows the phosphorylation of BAD in muscle tissue from Sprague-Dawley rats treated with a high glycine diet. Lane 1: Molecular Weight Marker; Lane 2: Akt-phosphorylated BAD as positive control; Lane 3: Phosphorylated BAD from control rat; Lane 4: Phosphorylated BAD from rats fed 5% glycine diet; Lane 5: Phosphorylated BAD from a rat fed 5% glycine diet Lane 6: Phosphorylated BAD from a rat fed 15% glycine diet).

FIG. 14 shows results of dual labeling experiments of proteins labeled with Cy3 fluorophore obtained from the adipose tissue of control animals.

FIG. 15 shows results of dual labeling experiments of proteins labeled with Cy3 fluorophore obtained from the adipose tissue of animals treated with 20% glycine in the diet. Yellow circles indicate down regulation versus control while red circles indicate up regulation as discernible through visual inspection.

FIG. 16A-B shows representative results of the LC/MS method of the quantification of glycine. FIG. 16A Top tracing is the composite TIC (Total Ion Current) obtained for glycine, proline, phenylalanine, lysine and leucine each at 78.125 pM on column. Middle tracing is the extracted TIC chromatogram for glycine. The bottom tracing is that obtained by composite wavelength monitoring by PDA (Photo Diode Array). FIG. 16B shows the standard curve obtained for glycine when the area under the peak of the extracted TIC for glycine is utilized to construct the calibration curve. Triplicate injections at each calibration level were used in order to construct the calibration curve.

FIG. 18 shows the dose response of immature female rat weight to glycine.

FIG. 19 shows the dose response of immature female rat length to glycine.

FIG. 20 shows the dose response of immature male rat weight to glycine.

FIG. 21 shows the dose response of immature male rat length to glycine.

DETAILED DESCRIPTION OF THE INVENTION

Figure 1:
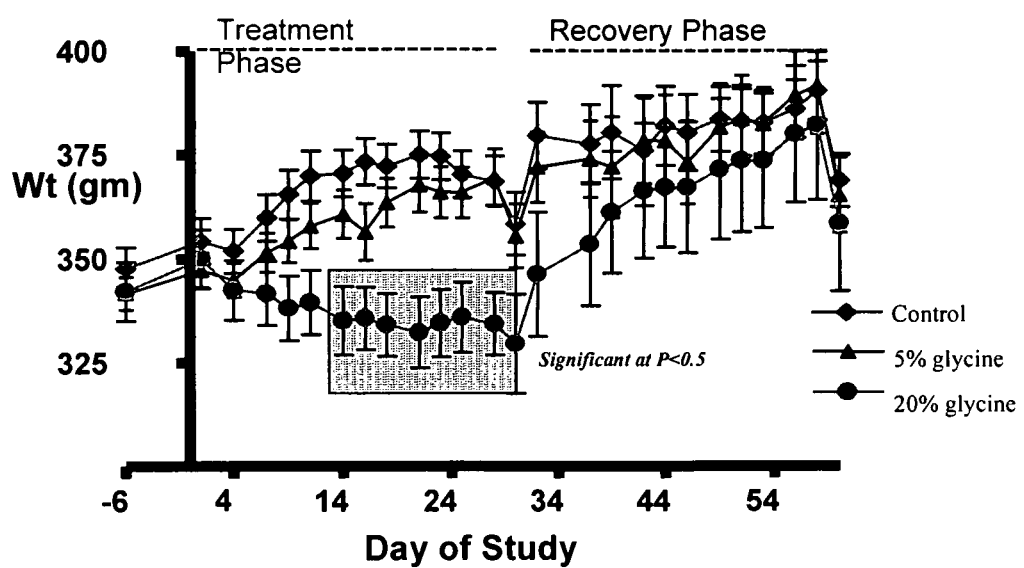
FIG. 1 shows the effect of a 5% glycine diet, a 20% glycine diet, and a non-supplemented diet on weight in adult male Fisher rats.

It has been discovered that a common amino acid, glycine, which when added to the diet of laboratory animals has the effect of causing a dose-dependent loss in weight. The effect has been observed in a number of rodent strains and in dogs. At optimal doses, and indeed at super-optimal doses, no deleterious side-effects were observed during prolonged administration. Glycine is a non-essential amino acid synthesized by most mammals from serine that arises from the glycolytic pathway as part of normal intermediary metabolism. It is a compound that has been extensively studied in its native and derivative forms with regard to its role in the origin and possible treatment of several mental disorders, particularly schizophrenia (see, e.g, Waziri & Baruah, *A hyperglycinergic rat model for the pathogenesis of schizophrenia: preliminary findings*. Schizophr Res, 1999. 37(3):205-15; Waziri, *Glycine therapy of schizophrenia*. Biol Psychiatry, 1988. 23(2):210-1; Waziri, *Glycine therapy of schizophrenia: some caveats*. Biol Psychiatry, 1996. 39(3):155-6; Javitt, *Glycine therapy of schizophrenia*. Biol Psychiatry, 1996. 40(7):684-6; Javitt, *Glycine modulators in schizophrenia*. Curr Opin Investig Drugs, 2002. 3(7):1067-72; Shoham et al., *Chronic high-dose glycine nutrition: effects on rat brain cell morphology*. Biol Psychiatry, 2001. 49(10):876-85; Javitt, *Management of negative symptoms of schizophrenia*. Curr Psychiatry Rep, 2001. 3(5):413-7; Shoham et al., *High dose glycine nutrition affects glial cell morphology in rat hippocampus and cerebellum*. Int J Neuropsychopharmcol, 1999. 2(1):35-40; Shoham, et al., *Glycine and D-cycloserine attenuate vacuous chewing movements in a rat model of tardive dyskinesia*. Brain Res, 2004. 1004(1-2):142-7; Tuominen et al., *Glutamatergic drugs for schizophrenia: a systematic review and meta-analysis*. Schizophr Res, 2005. 72(2-3):225-34). In several of these reports, an effect of glycine administration is noted to have a small but significant impact on weight of test animals or subjects, but this observation never became the subject of speculation or further analysis. This is probably because the observed effects were relatively small, no doubt due to the fact that the concentrations and times of exposure to glycine utilized in these studies were typically lower that those that we found were required to induce significant or dramatic weight loss. Petzke et al. (1987) reported that glycine has a relatively high thermogenic effect as compared to other amino acids, sugars and fats, which correlated with increased oxygen uptake. Petzke & Albrecht, [*The effect of nutrition on the metabolism of glycine*]. Nahrung, 1987. 31(2):157-72; Petzke et al., *Utilization of [1-14 C]carbon of glycine of high glycine diet fed young and old rats*, Zfa, 1987. 42(6): p. 323-8; Petzke et al., [*The effect of oral administration of glycine on metabolism*]. Nahrung, 1987. 31(3): p. 207-15. His group noted a dose-dependent reduction in the growth of experimental rats, but was not able to provide a biochemical basis for the possible mechanism. In addition to replicating this finding, as described below, we have demonstrated that adult animals show a dose-dependent weight loss with glycine supplementation of their diets. Glycine or glycine analogs can be used to combat obesity without observable adverse side-effects. Additionally, glycine acts to induce apoptosis specifically in adipose cells, probably using a heretofore unrecognized pathway.

Glycine and Glycine Analogs

Glycine is a readily available, non-toxic amino acid. Glycine, glycine analogs, or a combination thereof can be used in the methods of the invention. Any glycine analog that induces apoptosis, directly or indirectly, in adipose cells, such as white adipose cells can be used. In one embodiment of the invention a glycine analog can comprise Formula I.

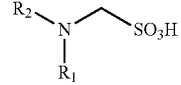

Formula I

For example, in Formula I: R1 and/or R2 can be a H;

R1 and/or R2 can be a Me, Et, or Pr;

R1 and/or R2 can be a Bn;

R1 and/or R2 can be a $(CH_2)_{2-5}$;

Formula I can be synthesized by, for example, the following scheme:

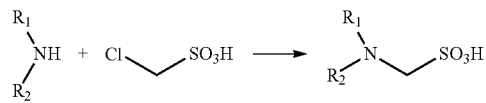

Other glycine analogs can comprise Formula II:

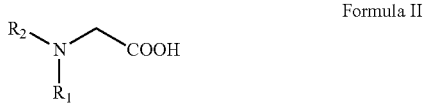

Formula II

For example, in Formula II: R1 and/or R2 can be a H;
R1 and/or R2 can be a Me, Et, or Pr;
R1 and/or R2 can be a Bn;
R1 and/or R2 can be a $(CH_2)_{2-5}$;
Formula II can be synthesized by, for example, the following scheme:

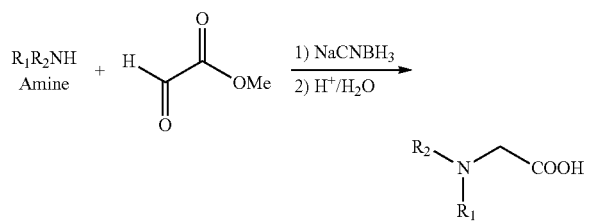

In another embodiment of the invention glycine analogs can comprise Formula III:

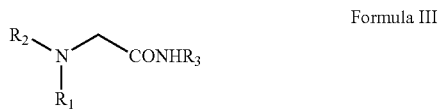

Formula III

In Forumula III: R1 and/or R2 can be H, and R3 can be H, Me, Et, Pr, or Bn;
R1 and/or R2 can be Me, Et, or Pr, and R3 can be Me, Et, Pr, or Bn;
R1 can be H; R2 can be Bn or Me, and R3 can be Me, Et, Pr, or Bn;
R1 and/or R2 can be $(CH_2)_{2-5}$ or Me, R3 can be Me, Et, Pr, or Bn.

Formula III can be synthesized by, for example, the following scheme:

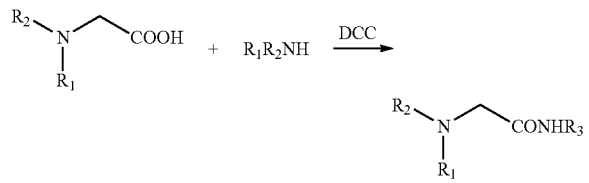

High Glycine Diet

A "high glycine diet" is a diet high in glycine, a glycine analog or analogs, or combinations thereof, or high dosages of glycine supplements, glycine analog supplements or combinations thereof. In one embodiment of the invention glycine analogs or glycine analogs combined with glycine produces a physiologic effect about the same as that obtained when a diet comprising only glycine is administered. That is, glycine analogs or the combination of glycine and glycine analogs produce a physiologic concentration of glycine in the animal that is about the same as the physiologic concentration of glycine in the animal when glycine is administered to the animal in a high glycine diet. In some instances glycine analogs or glycine analogs in combination with glycine can be administered at a lower percentage than glycine alone to achieve a similar effect as when glycine is used alone. For example, glycine analogs or glycine analogs in combination with glycine can be administered in a diet at about 1,2,3,4,5,6,7,8,9,10, percent or more by weight.

The glycine and glycine analogs can be mixed into the diet or administered by other routes. The supplements can be liquid, semi-solid, solid or any other form. A high glycine diet comprises about 5, 6, 7, 8, 9, 10, 11, 12, 13, 14, 15, 16, 17, 18, 19, 20, 25, 30, 35, 40%, or more by weight of glycine, glycine analogs or combinations thereof. In one embodiment of the invention a high glycine diet can comprise about 5% to about 40% or more, about 10% to about 40%; about 10% to about 30%; about 15% to about 25%; or about 20% to about 25% glycine, or glycine analogs or combinations thereof.

The invention also provides a diet composition for weight reduction in an animal comprising about 5% to about 40% or more, about 5% to about 40%; about 10% to about 30%; about 15% to about 25%; or about 20% to 25% glycine, glycine analogs or combinations thereof (i.e., about 5, 6, 7, 8, 9, 10, 11, 12, 13, 14, 15, 16, 17, 18, 19, 20, 25, 30, 35, 40%, or more by weight of glycine, glycine analogs or combinations thereof) and about 60% to about 95% (i.e., about 95, 90, 89, 88, 87, 86, 85, 84, 83, 82, 81, 80, 75, 70, 65, or 60%) of a diet that is low in calories.

The invention also provides a diet composition for weight reduction in an animal comprising about 5% to about 40% or more; about 10% to about 40% or more; about 10% to about 30%; about 15% to about 25%; or about 20% to 25% glycine, glycine analogs or combinations thereof. (i.e., about 5, 6, 7, 8, 9, 10, 11, 12, 13, 14, 15, 16, 17, 18, 19, 20, 25, 30, 35, 40%, or more by weight of glycine, glycine analogs or combinations thereof) and about 60% to about 95% (i.e., about 95, 90, 89, 88, 87, 86, 85, 84, 83, 82, 81, 80, 75, 70, 65, or 60%) of a diet that is low in fat. The low-fat diet can be a low saturated fat diet.

The invention also provides a diet composition for weight reduction in an animal comprising about 5% to about 40% or more; 10% to about 40% or more; about 10% to about 30%; about 15% to about 25%; or about 20% to 25% glycine, glycine analogs or combinations thereof (i.e., about 5, 6, 7, 8, 9, 10, 11, 12, 13, 14, 15, 16, 17, 18, 19, 20, 25, 30, 35, 40%, or more by weight of glycine, glycine analogs or combinations thereof) and about 60% to about 95% (i.e., about 95, 90, 89, 88, 87, 86, 85, 84, 83, 82, 81, 80, 75, 70, 65, or 60%) of a diet that is low in carbohydrates.

Methods of the Invention

The administration of high glycine diet to a male or female animal, such as a human, can induce apoptosis in adipose tissue, in particular, white adipose tissue of the animal. Therefore, the high glycine diet can reduce adipose tissue or reduce adipose cell size or both in the animal. Methods of the invention comprise administering a high glycine diet to an animal to induce apoptosis in adipose tissue, reduce adipose tissue, reduce adipose cell size, or combinations thereof in the animal.

While not wishing to be bound to a particular theory, it is believed that the induction of apoptosis in adipose tissue is caused by the direct or indirect effect of glycine. This mechanism of action is supported by the observed effects that such a diet has on BAD, a pro-apoptotic member of the Bcl-2 family. BAD's ability to promote cell death is inhibited by phosphorylation at position 136. The administration of a high glycine diet reduces or eliminates phosphorylation of BAD at position 136 in adipose tissue indicating that the loss of adipose tissue observed when a high glycine diet or its equivalent is administered occurs through induction of apoptosis.

The administration of a high concentration of glycine either in the diet (i.e., orally) or via other means of administration can reduce abdominal fat content in an animal. Additionally, the administration of glycine either in the diet or via other means of administration to an animal can produce weight loss in the animal. However, upon initial administration of a diet supplemented with glycine, a weight gain may be seen. While not wishing to be bound by any particular theory, it is believed that this observation may be a result of the loss of fat tissue and the gain of muscle tissue.

The methods and compositions of the invention can be used to produce reduced-sized and or reduced-weight animals. For example, animals that are about 3%, 5%, 10%, 20%, 30%, 40%, 50%, 60%, 70%, or 75% smaller than normal-sized animals or about 3%, 5%, 10%, 20%, 30%, 40%, 50%, 60%, 70%, or 75% lighter than normal-weight animals. A normal-sized or normal-weight animal is an animal that falls within an average or typical weight or size range for the animal species where age and general health condition are taken into account.

The invention provides methods for producing reduced-sized, or reduced-weight, or both reduced-size and reduced-weight animals comprising administering to the animal a high glycine diet. For reduced-size animals, a high glycine diet is fed to immature animals. The high glycine diet can be administered on a daily basis. The animal can be, for example a human, non-human primate, a rat, a mouse, a rabbit, a guinea pig, a bovine, a pig, a sheep, a goat, a dog, a cat, a horse, a bird or a fish.

The invention also provides methods for producing a reduced-sized animal as described above followed by returning the animal to a normal size. The methods comprise administering a high glycine diet to an immature animal to produce a reduced-sized animal and then administering a normal diet to the animal to produce a normal-sized animal. A normal diet is a diet that is not supplemented with glycine, but contains normal amounts of glycine.

The invention also provides methods for producing a reduced-weight animal and then returning the animal to a normal weight comprising administering a high glycine diet to the mature or immature animal to produce a reduced-weight animal and then administering a normal diet to the animal to produce a normal-weight animal.

Yet another embodiment of the invention provides a method for producing a permanently reduced-sized and or reduced-weight animal through the administration of a high glycine diet to an immature animal to produce a permanently reduced-sized or reduced weight animal. Administration of a high glycine diet can be continued throughout the lifetime of the animal or until further growth is prevented by the physiological processes that normally are associated with cessation of growth.

Methods and compositions of the invention can also be used to produce weight loss in an animal such as an immature or mature animal. Weight loss of about 3%, 5%, 10%, 20%, 30%, 40%, 50%, 60%, 70%, or 75% can be achieved.

One embodiment of the invention provides a method for producing weight loss in an animal comprising administering to the animal a high glycine diet as described above. The animal can be, for example, a human, a non-human primate, a rat, a mouse, a rabbit, a guinea pig, a bovine, a pig, a sheep, a goat, a dog, a cat, a horse, a bird, a fish or an invertebrate. In one embodiment of the invention, the animal is healthy and has no underlying health problems or issues. In another embodiment of the invention the animal has only an over-weight or obesity health problem and no other health problems or issues.

A high glycine diet can be administered with an adjunctive weight loss therapy such as an exercise regimen, a low-fat diet, a low-calorie diet, a low-carbohydrate diet, surgical intervention such as gastroplasty, gastric partitioning, and gastric bypass, behavioral therapy, pharmacotherapy (e.g., use of sibutramine, MERIDIA® (sibutramine HCl monohydrate), XENICAL® (orlistat) and combinations thereof), natural dietary aids or over the counter (OTC) weight-loss products, and combinations thereof.

A low-fat diet is a diet that comprises about 3%, 5%, 10%, 15%, 20%, 25%, 30%, 40%, 50%, 60%, 70% or 80% less fat than the normal recommended amount of fat in a diet for a given species of a given age, weight, and general health condition. For example, a low-fat diet in humans can comprise a diet consisting of about 0%, 3%, 5%, 7%, 10%, 13%, 15%, 20% or 25% fat.

A low-calorie diet is a diet that comprises about 3%, 5%, 10%, 15%, 20%, 25%, 30%, 40%, 50%, 60%, 70% or 80% less calories than the normal recommended amount of calories for a certain species of a given age, weight, and general health condition.

A low carbohydrate diet is a diet that comprises about 3%, 5%, 10%, 15%, 20%, 25%, 30%, 40%, 50%, 60%, 70% or 80% less carbohydrates than the normal recommended amount of calories for a certain species of a given age, weight, and general health condition.

Behavior therapy includes strategies that help in overcoming barriers to compliance with dietary therapy and/or exercise therapy. Such strategies include, for example, self-monitoring of eating habits and exercise, stress management, stimulus control, problem-solving (e.g., self-corrections of problem areas related to eating and exercise), contingency management (e.g., use of rewards for specific desirable actions, cognitive restructuring (e.g., modification of unrealistic goals and inaccurate beliefs), and social support.

Glycine and glycine analogs can be administered, for example, orally, topically, parenterally, by inhalation or spray, or rectally using formulations containing conventional non-toxic pharmaceutically acceptable carriers, adjuvants and/or vehicles. The term parenteral as used herein includes percutaneous, subcutaneous, intravascular (e.g., intravenous), intramuscular, or intrathecal injection or infusion techniques and the like. In addition, glycine and glycine analogs can be combined with a pharmaceutically acceptable carrier. Glycine and glycine analogs can be present in association with one or more non-toxic pharmaceutically acceptable carriers, excipients, coloring agents, preservative agents, flavoring agents, diluents, adjuvants or combinations thereof, and if desired other active ingredients. Glycine and glycine analogs can be in any form suitable for oral use, for example, as tablets, troches, lozenges, aqueous or oily suspensions, dispersible powders or granules, emulsion, hard or soft capsules, or syrups or elixirs.

Another embodiment of the invention provides a method of inducing apoptosis in a white adipocyte, in vivo or in vitro, comprising administering one or more glycine analogs or a combination of glycine and glycine analogs to the adipocyte.

Even another embodiment of the invention provides a method of reducing phosphorylation of BAD at amino acid position 136 in a white adipocyte, in vivo or in vitro, comprising administering a one or more glycine analogs or a combination of glycine and glycine analogs to the adipocyte.

Glycine can be added to an adipocyte at a concentration of about 5, 10, 50, 75, 100, 200, 300, 400, 500, 750, 1000 µg/ml or more.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while maintaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Rats were randomly divided, caged separately, and fed water ad libitum and diet TD 80406 diet (Harlan Teklad, Madison, Wis.). The diet composition is shown in Table 1. The TD 80406 diet has about 1-2% glycine present in the lactalbumin component and is considered a non-supplemented diet.

TABLE 1

TD 80406 Diet

|  | g/kg |
| --- | --- |
| Lactalbumin (New Zealand Milk Products) | 200.0 |
| Corn Starch | 620.0 |
| Powdered Confectioners Sugar | 50.0 |
| Cottonseed Oil | 30.0 |
| Cellulose | 60.0 |
| Mineral Mix, MIT 200 (Teklad TD 70191) | 30.0 |
| Vitamin Mix, (Teklad 40060) | 10.0 |

Adult (180 day old) male Fisher rats were randomly assigned in treatment groups of 10 rats in each group to diets comprising 5% or 20% glycine in their feed or a non-supplemented diet. See FIG. 1. Animal and food weight measurements were obtained on the indicated day of the study. The analyst undertaking the weight measurement was blinded relative to the diet of the animal for which the observation was being recorded. The bars represent ±1 standard error of the weights of the rats in each group on the indicated observation day. Rats fed a 20% glycine diet were statistically lighter than the rats fed a 5% glycine diet or a diet that is not supplemented with glycine during the 14-30 day period of the treatment. Once the rats fed a 20% glycine diet were returned to a non-supplemented diet on day 30, they rapidly gained weight and their weights became similar to that of rats fed a non-supplemented diet. There was no statistical difference between the weights of the animals in the control and the 20% glycine group after day 32 of the studies.

Figure 2:
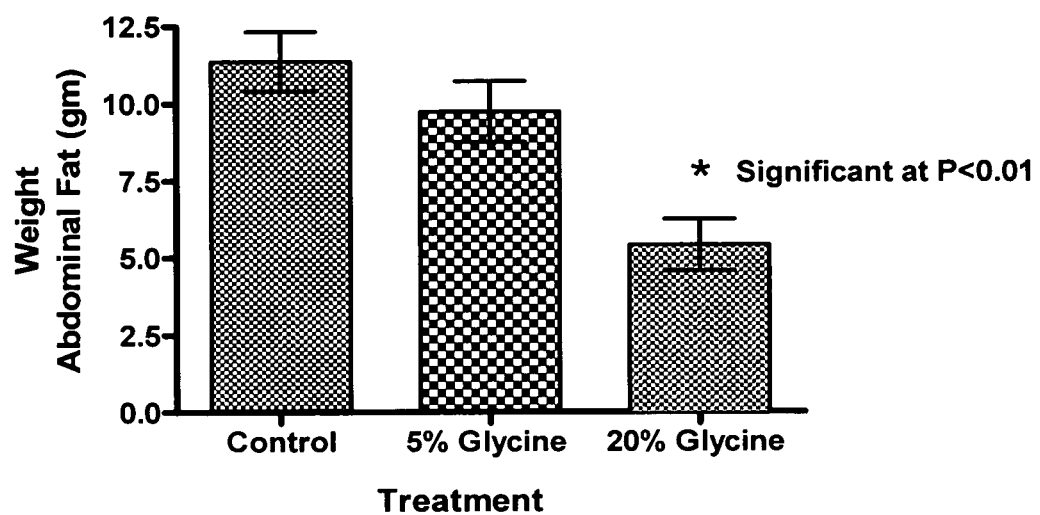
FIG. 2 shows the effect of a 5% glycine diet, a 20% glycine diet, and a non-supplemented diet on abdominal fat content in adult male Fisher rats.

Five rats from each treatment group were chosen at random and euthanized on day 30 of the study. Measurements of the abdominal fat content of each rat were obtained at necropsy (FIG. 2). The analyst undertaking the measurement was blinded relative to the treatment group of the animal for which the observation was being recorded. Data was analyzed using a One-Way Analysis of Variance and subjected to post-hoc analysis using Dunnett's Multiple Comparison Test. The rats fed a 20% glycine diet had statistically significant less abdominal fat than those that were fed a 5% glycine diet or a non-supplemented diet.

Figure 3:
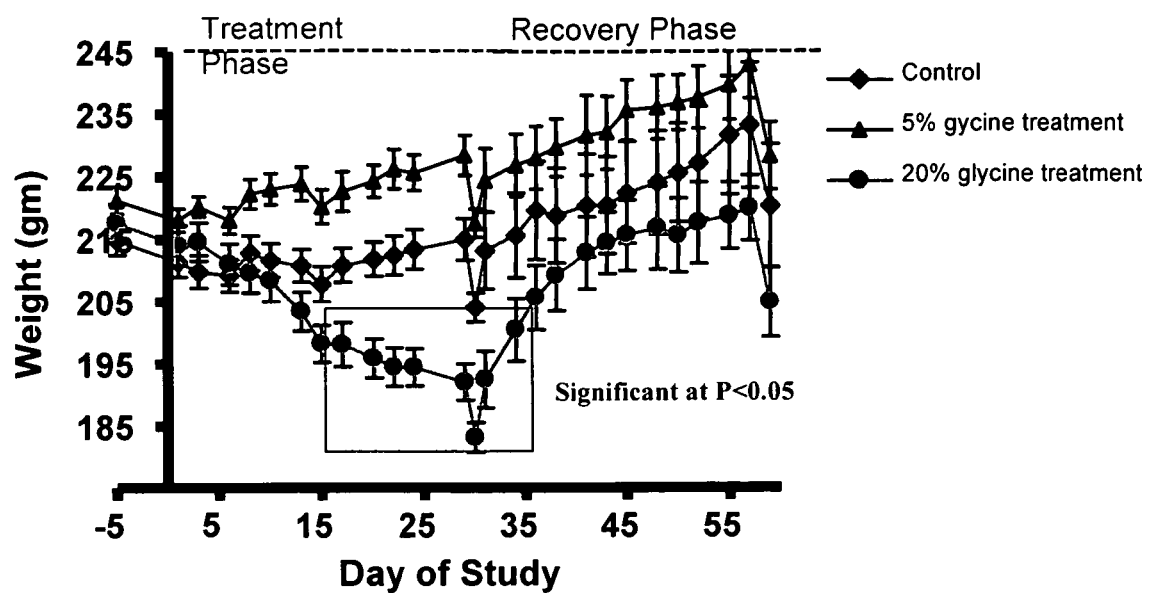
FIG. 3 shows the effect of a 5% glycine diet, a 20% glycine diet, and a non-supplemented diet on the weight of adult female Fisher rats.
Figure 4:
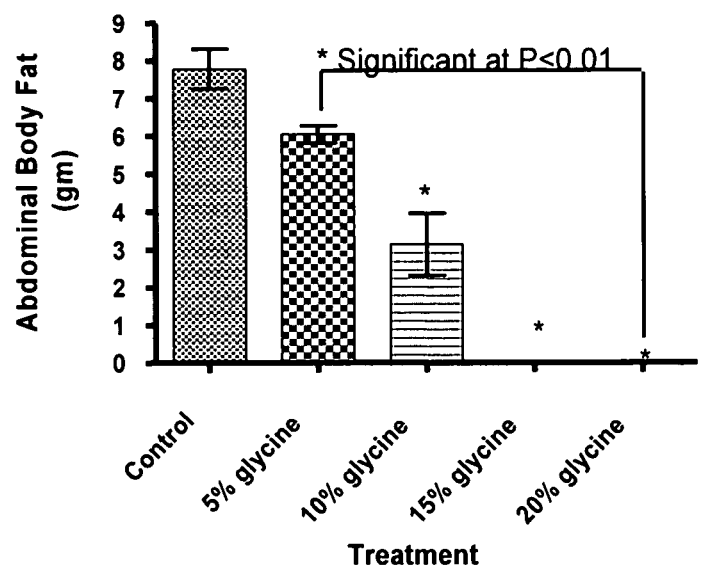
FIG. 4 shows the effect of a 5% glycine diet, a 20% glycine diet, and a non-supplemented diet on abdominal fat content in adult female Fisher rats.

The identical experiment was performed with female adult (180 day old) Fisher rats. The results obtained were generally similar except that the effect of glycine was actually somewhat more pronounced in the females than in the males, both in regard to weight loss and abdominal fat content (FIG. 3 and FIG. 4). It was noted that the weight of the treated female rats did not rebound to the level of the control animals by the end of the Recovery Phase and that the reduction observed in abdominal fat was greater than that observed for the male. No significant differences were observed between groups in the amounts of food or water consumed throughout the course of the experiment.

Figure 5:
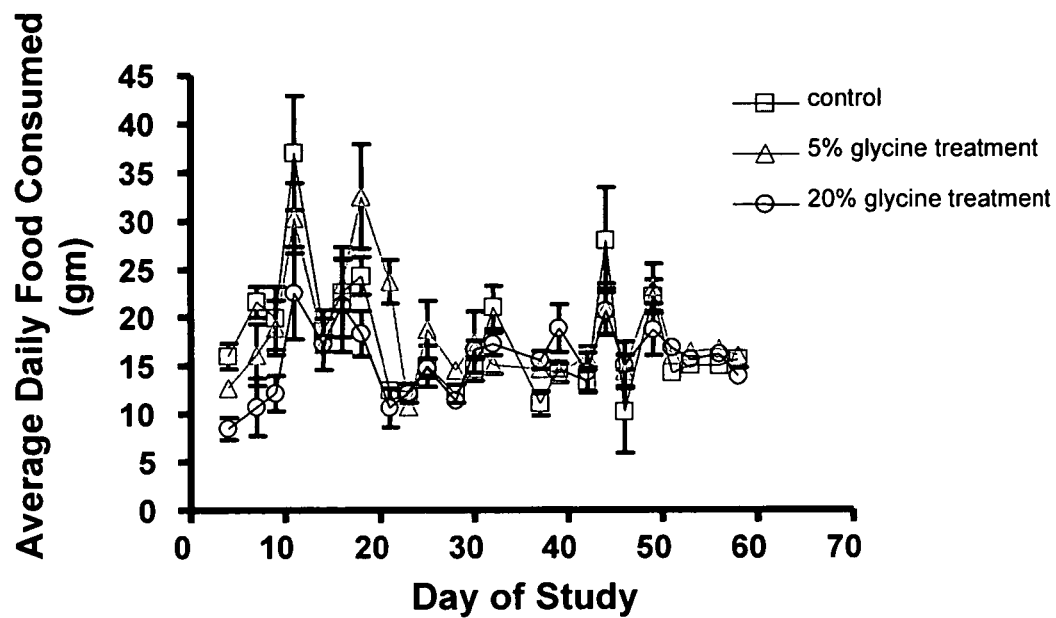
FIG. 5 shows the effect of a 5% glycine diet, a 20% glycine diet, and a non-supplemented diet on food consumption in adult male Fisher rats.

Food consumption measurements were obtained on the indicated days of study. See FIG. 5. These data indicate that the observed weight loss is not a result of caloric restriction due to reduced food intake. Additionally, the observed weight reduction is not a result of reduced caloric content of the food as the diets were analyzed by bomb-calorimetry (see Table 2) and demonstrated to not be significantly different in caloric content.

TABLE 2

Caloric Content of TD 80406 diet (Harlan Teklad, Madison, Wisconsin) Supplemented With Indicated Amount of Glycine

| Sample ID | Results (cal/g) |
| --- | --- |
| Harlan TD 80406 Control Diet 0% Glycine Supplementation | 4189.7 |
| Harlan TD 80406 Control Diet 5% Glycine Supplementation | 2987.8 |
| Harlan TD 80406 Control Diet 10% Glycine Supplementation | 4094.3 |
| Harlan TD 80406 Control Diet 15% Glycine Supplementation | 3716.9 |
| Harlan TD 80406 Control Diet 20% Glycine Supplementation | 3859.5 |

Blood samples were withdrawn from the tail vein of the rats under study and sent to Charles River Laboratories for Mutli-Analyte Profile testing. The results of these tests indicated that those rats on a high glycine diet exhibited statistically significant (p≤0.05) reduction in their serum triglyceride, HDL and cholesterol levels. These results correspond with results in the literature by others performing research with glycine. See, Hafidi et al., *Glycine intake decreases plasma free fatty acids, adipose cell size, and blood pressure in sucrose-fed rats*. Am J Physiol Regul Integr Comp Physiol, 2004. 287(6):R1387-93; Aust et al., *The hypolipaemic action of a glycine rich diet in rats*. Nahrung, 1980. 24(7):663-71; Sugiyama et al., *Dietary sulfur-containing amino acids and glycine as determinant factors in plasma cholesterol regulation in growing rats*. J Nutr Sci Vitaminol (Tokyo), 1985. 31(1):121-5; Senthilkumar et al., *Glycine modulates hepatic lipid accumulation in alcohol-induced liver injury*. Pol J Pharmacol, 2003. 55(4): 603-11; Park et al., *Dietary taurine or glycine supplementation reduces plasma and liver cholesterol and triglyceride concentrations in rats fed a cholesterol-free diet*. Nutrition Research, 1999. 19(12):1777-1789; Yoshida et al., *Effects of addition of arginine, cystine, and glycine to the bovine milk-simulated amino acid mixture on the level of plasma and liver cholesterol in rats*. J Nutr Sci Vitaminol (Tokyo), 1988. 34(6):567-76; Olson et al., *Effect of amino acid diets upon serum lipids in man*. Am J Clin Nutr, 1970. 23(12): 1614-25; Ryzhenkov et al., [*Hypolipidemic activity of glycine and its derivatives*]. Vopr Med Khim, 1984. 30(2):78-80; Yagasaki et al., *Effects of dietary methionine, cystine, and glycine on endogenous hypercholesterolemia in hepatoma-bearing rats*. J Nutr Sci Vitaminol (Tokyo), 1986. 32(6):643-51; Emi et al., *Missense mutation (Gly-Glu188) of human lipoprotein lipase imparting functional deficiency*. J Biol Chem, 1990. 265(10):5910-6. Decrease in leptin levels, trending toward significance were observed, as would be expected when white adipose tissue (WAT) is decreased. Adiponectin levels were observed to increase in a manner trending towards significance as would be expected when WAT is decreasing. The data demonstrated that a high glycine diet resulted in a positive effect on these biomarkers of pathogenicity of obesity.

Example 2

Figure 6:
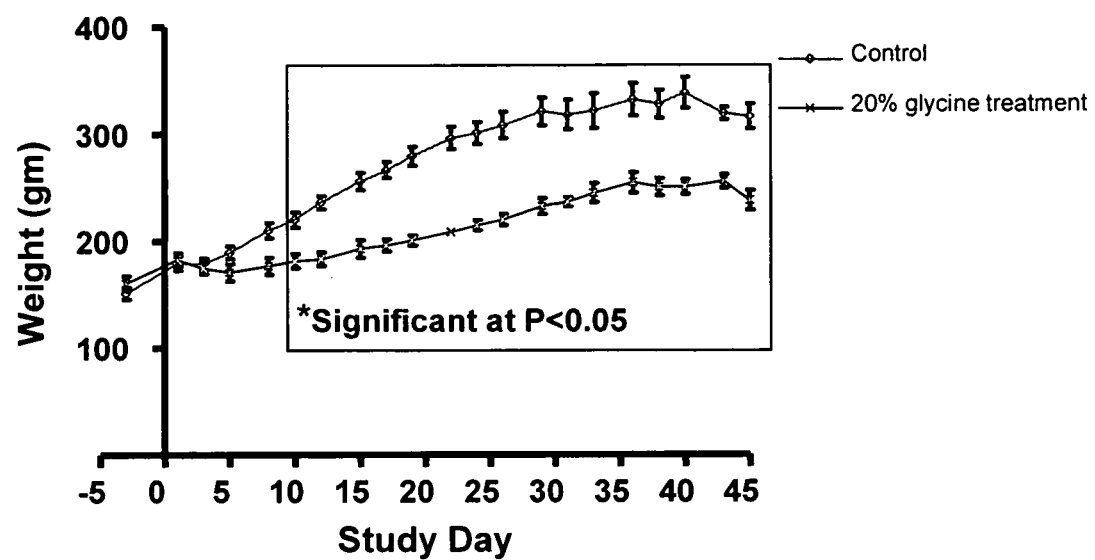
FIG. 6 shows the effect of a 20% glycine diet and a non-supplemented diet on the weight of male ZDF rats.
Figure 7:
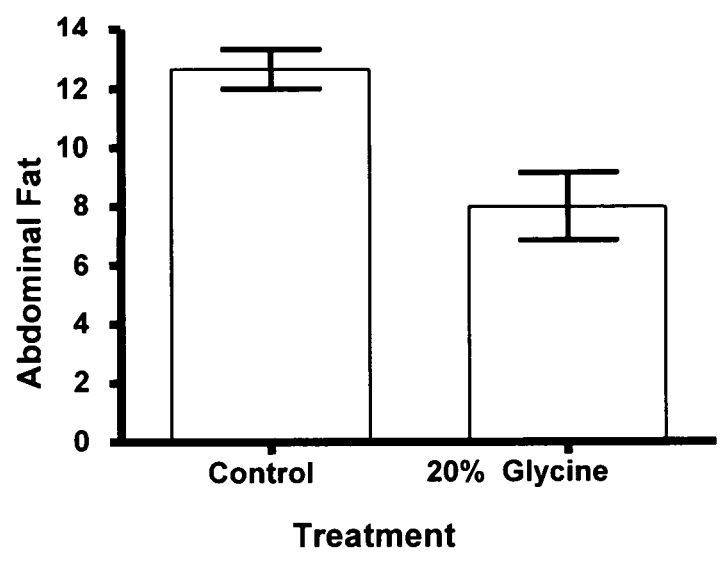
FIG. 7 shows the effect of a 20% glycine diet and a non-supplemented diet on ZDF rat abdominal fat content.

Adult male Zucker diabetic fatty (ZDF) rats were randomly assigned in treatment groups of 3 rats in each group to diets comprising 20% glycine in their feed or a non-supplemented diet. ZDF rats are obese, hyperlipidemic, and insulin resistant. Weight measurements were obtained on the indicated day of the study. See FIG. 6. The analyst undertaking the weight measurement was blinded relative to the diet of the animal for which the observation was being recorded. The bars represent±1 standard error of the weights of the rats in each group on the indicated observation day. Data was analyzed using a One-Way Analysis of Variance and subjected to post-hoc analysis using Dunnett's Multiple Comparison Test. Rats fed a 20% glycine diet had statistically significant decrease in weight from day 15 through day 36 of the study relative to rats fed a non-supplemented diet. Again, no difference was observed between groups in food consumption. Measurements of the abdominal fat content of each rat were obtained at necropsy (FIG. 7). The rats fed a 20% glycine diet had statistically significant (p≤0.05) less abdominal fat than those that were fed a 5% glycine diet or a non-supplemented diet.

Example 3

Figure 8:
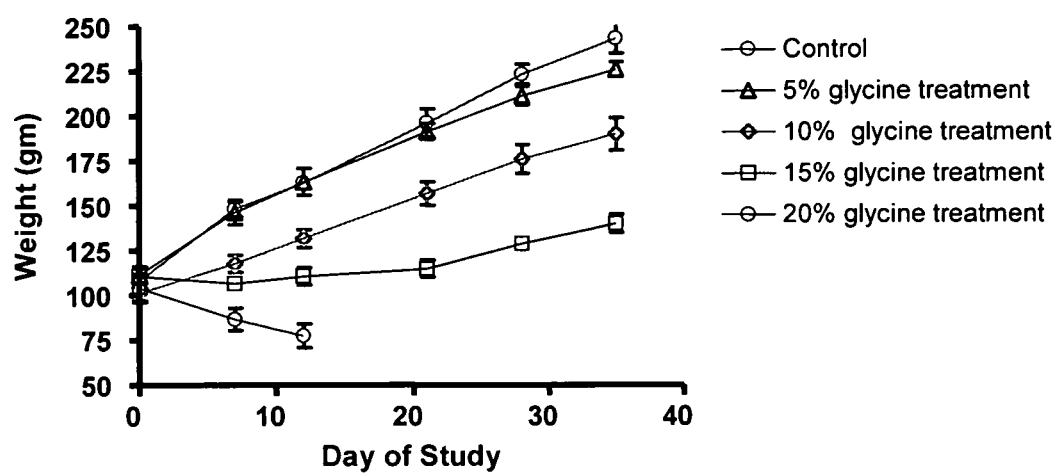
FIG. 8 shows the effect of a 5%, 10%, 15%, and 20% glycine diet, and a non-supplemented diet on the weight of female Sprague-Dawley rats.

Adult female Sprague-Dawley rats were randomly assigned in treatment groups of 3 rats in each group to diets comprising 5, 10, 15, or 20% glycine in their feed or a non-supplemented diet. See FIG. 8. Weight measurements were obtained on the indicated day of the study. The analyst undertaking the weight measurement was blinded relative to the diet of the animal for which the observation was being recorded. The bars represent±1 standard error of the weights of the rats in each group on the indicated observation day. The weights of the rats fed a 20% glycine diet were less than that of the rats fed a non-supplemented diet. Data was analyzed using a One-Way Analysis of Variance and subjected to post-hoc analysis using Dunnett's Multiple Comparison Test. Rats fed a 20% glycine diet had statistically significant decrease in weight from day 15 through day 36 of the study relative to rats fed a non-supplemented diet.

Example 4

Figure 9:
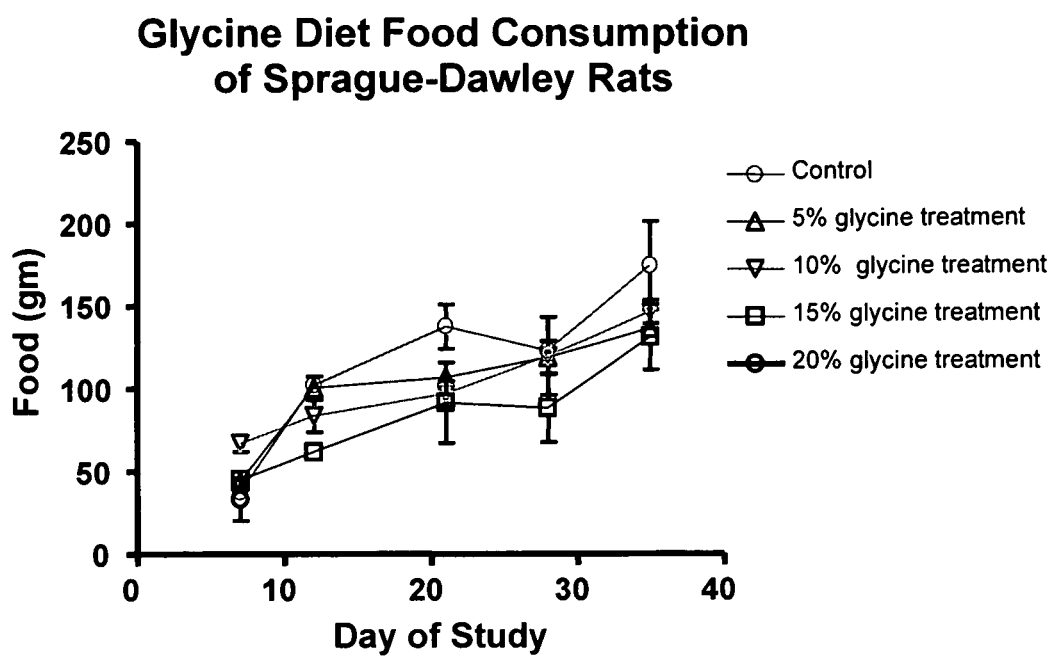
FIG. 9 shows the effect of a 5%, 10%, 15%, and 20% glycine diet, and a non-supplemented diet on food consumption of Sprague-Dawley rats

Adult female Sprague-Dawley rats were randomly assigned in treatment groups of 3 rats in each group to diets comprising 5, 10, 15, or 20% glycine in their feed or a non-supplemented diet. See FIG. 9. Food consumption measurements were obtained on the indicated days of study. The analyst undertaking the measurement was blinded relative to the diet of the animal for which the observation was being recorded. These data indicate that the observed weight loss is not a result of caloric restriction due to reduced food intake. Additionally, the observed weight reduction is not a result of reduced caloric content of the food as the diets were analyzed by bomb-calorimetry (See Table 2) and demonstrated to not be significantly different in caloric content.

Example 5

Adult female Sprague-Dawley rats were randomly assigned in treatment groups of 3 rats in each group to diets comprising 5, 10, 15, or 20% glycine in their feed or a non-supplemented diet. The rats in each treatment group were euthanized on day 30 of the study. Measurements of the abdominal fat content of each rat were obtained at necropsy. See FIG. 10. The analyst undertaking the measurement was blinded relative to the treatment group of the animal for which the observation was being recorded. Data was analyzed using a One-Way Analysis of Variance and subjected to post-hoc analysis using Dunnett's Multiple Comparison Test. The rats fed a diet containing the indicated amounts of glycine from 5% to 20% had statistically significant less abdominal fat than those that were fed a non-supplemented diet.

Example 6

Sprague Dawley rats, 24 days old, were fed a diet of 15% glycine and 85% TD80406. No gross lesions or treatment related abnormalities other than weight were reported at necropsy of animals fed diet containing 15% glycine and 85% TD80406 for 6 weeks. No differences in blood chemistry and complete blood counts were observed between control animals fed 100% TD80406 and animals fed a diet containing 15% glycine and 85% TD80406 for 6 weeks. Histopathological examination of tissues harvested from one animal fed a diet supplemented with high glycine was performed. A microscopic examination of trimmed, processed, embedded, microtomed, and hematoxylin and eosin stained tissues revealed no remarkable results for the brain, lung, liver, adrenal gland, kidneys, urinary bladder, heart, stomach, large intestine, or small intestine. In short, there were no microscopic changes from normal histology.

Example 7

Adult male Sprague-Dawley rats were randomly assigned in treatment groups of 3 rats in each group to diets comprising 5% or 20% of glycine in their feed or a non-supplemented diet. On day 20 of the study the animals were euthanized and the adipose tissue obtained at necropsy. Total proteins were extracted from the adipose tissue. In order to demonstrate that adipose tissue derived from rats fed a high glycine diet underwent apoptosis, extracts of animals fed control or glycine-containing diets were assayed for the ability to phosphorylate BAD at position 136. As seen in FIGS. 11A and 11B the data clearly demonstrated a dose dependent decrease in the phosphorylation of BAD at tyrosine 136 in (WAT) while no such decrease was observed in brown adipose tissue (BAT), indicating that a high glycine diet leads to apoptosis in white adipose tissue. FIG. 12 and FIG. 13 clearly demonstrate that no such decrease in the phosphorylation state of BAD at tyrosine 136 was observed when extracts of liver tissue (FIG. 12) or muscle (FIG. 13) from the same animal were assayed.

The data clearly demonstrated a dose dependent decrease in the phosphorylation of BAD at tyrosine 136, indicating that a high glycine diet leads to apoptosis in adipose tissue.

Assay of the tissue extracts for the ability to phosphorylate BAD at serine position 136 was performed as follows: One mg of tissue extract was added to BAD agarose (Upstate, Waltham, Mass.). The reaction volume was adjusted to 1 ml using RIPA buffer (with anti-phosphatases and anti-proteases) (Tris-HCl [pH 7.4] 50 mM; NP-40 1%; Na deoxycholate 0.25%; NaCl 150 mM; EDTA 1 mM; PMSF 1 mM; Protease Arrest 100 ul; sodium orthovanadate 1 mM; sodium fluoride 1 mM) and incubated for 0.5 hr at 30° C. The agarose beads were collected by centrifugation (5 sec at 12,000× g). The supernatant was removed and the beads washed 3× with ice cold TBS. The BAD-agarose was resuspended in 40 µl of sample buffer, boiled for 5 min, and centrifuged (5 min at 12,000× g). Seven microliters of sample were electrophoresed on a 15% gel (Tris-Glycine). The protein was transferred by western blotting to a nitrocellulose membrane and blocked with 5% NFM in TTBS at 4° C. with shaking. The membrane was washed with 2% NFM in TTBS. Each lane was blotted with rabbit anti-phospho-BAD 136 antibody at (1:1000 in 2% NFM/TTBS) for 2 hrs at room temperature. The blots were washed three times for 5 min with TTBS. The blots were incubated with goat anti-Rabbit-HRP (1:5000 in 2% NFM/TTBS). The blots were washed 3× for 5 min with TTBS and 2× 5 min with TBS. Visualization of phosphorylated BAD was accomplished with a chemiluminesence substrate (Pierce Super-Signal Substrate™).

In order to further elucidate the mechanism of action by which glycine elicits the observed biological effects we used 2D-Differential in Gel Electrophoresis (2D-DIGE). 2D-DIGE is a powerful method that allows for the rapid assessment of differences in expression in proteomes of tissues from differing biological states. See, Patton, *Detection technologies in proteome analysis*. J Chromatogr B Analyt Technol Biomed Life Sci, 2002. 771(1-2):3-31; Unlu et al., *Difference gel electrophoresis: a single gel method for detecting changes in protein extracts*. Electrophoresis, 1997. 18(11):2071-7; Von Eggeling et al., *Fluorescent dual colour 2D-protein gel electrophoresis for rapid detection of differences in protein pattern with standard image analysis software*. Int J Mol Med, 2001. 8(4):373-7.

Preliminary results of dual labeling experiments of the proteins extracted from tissue obtained from control (FIG. 14) and 20% glycine treated (FIG. 15) were obtained in preparation for undertaking future 2D-DIGE experiments. Proteins labeled with Cy3 fluorophore obtained from the adipose tissue of control animals is presented in FIG. 14. FIG. 15 presents the results obtained with protein obtained labeled with Cy5 fluorophore from adipose tissue of animals treated with 20% glycine in the diet. Yellow circles indicate down regulation versus control while red circles indicate up regulation as discernible through visual inspection.

2D-DIGE analysis of adipose tissue from female Sprague-Dawley rats fed either a control diet or diet supplemented with 20% glycine by weight. Tissue samples were homogenized on ice using a PowerGen 125 Model FTH 115 Homogenizer fitted with 7X110 mini-Tip Reusable Generator Probes and the proteins extracted using a Total Protein Extraction (TPE) Kit (Genotech, 92-Weldon Parkway, St. Louis, Mo. 63043-9989 U.S.A.) according to the protocol supplied with the kit. All buffers contained Protease Arrest Cocktail (Genotech, 92-Weldon Parkway, St. Louis, Mo. 63043-9989 U.S.A.) in order to minimize protein degradation during extraction and storage prior to use. The extracted proteins were precipitated using Bio Rad 2D cleanup kit (Cat.#163-2130) and resuspended in Cy labeling buffer (30 mM Tris-HCl pH 8.5, 4% CHAPS, 8M urea). Equal amounts of protein (50 ug) obtained from the control animals and treated animals were each labeled with 400 pmol of Cy3 or Cy5 fluorophore diluted in DMF according to manufacturer's specifications. Labeling reactions were carried out in the dark for 30 min on ice and quenched by addition of 1 mM lysine. The two populations of labeled proteins were mixed with Biolyte ampholytes (Bio Rad cat.#163-1112) and rehydration buffer (Bio Rad cat. #163-2083). The mixture was then loaded onto rehydrated IPG strips (Bio Rad Cat.#163-2099) over night at room temperature. The proteins in the rehydrated IPG strips were focused on a Biorad Protean IEF Gel apparatus and run in the $2^{nd}$ dimension on a Bio Rad Protean Slab Gel apparatus according to the manufacturer's instructions. Visualization of the Cy3 and Cy5 labeled proteins in the gels was undertaken using a KODAK Image Station 2000 MM using 535 and 620 nm excitation and 600 and 670 nm emission filters respectively.

Example 8

Sensitive Assay for Accurate Measurement of the Concentration of Glycine in Blood and Tissues (Adipose)

The development of pharmacokinetic and pharmacodynamic models for glycine with respect to reduction of adipose tissue mass will require an accurate method for the measurement of the concentration of the administered glycine. Ideally, the method will be capable of following the adsorption, distribution, metabolism and excretion (ADME) of the administered glycine exclusive of endogenous glycine. Additionally, the method developed should be capable of being easily modified for application to future studies with the glycine analogs. A LC/MS method can be used for this purpose. This approach allows the utilization of $C_{13}$-Glycine in studies enabling the simultaneous determination of the ADME of dosed $C_{13}$-Glycine and endogenous glycine.

In brief, the methodology consists of a sample clean-up step wherein proteins and nucleic acid contaminants are removed by acid precipitation prior to analysis by LC/MS. QC-samples are prepared prior to the initiation of each study containing known amounts of glycine/$C_{13}$-Glycine in sample matrix (i.e. plasma or dialyzed tissue extract from untreated animals). Acid precipitation of the samples will be accomplished by the addition of 100 µl of an ice-cold 10% (vol/vol) perchloric acid containing 1% metaphosphoric acid to 100 µl of a plasma sample in a brown 1.5 ml microcentrifuge tube that is incubated on ice for 10 min prior to centrifugation at 12,000× g for 5 min at 4° C. The resultant supernatant will then be filtered through a 0.2 µm filter and dried in vacuo on a Savant SC110 Speedvac (or equivalent). The study and QC sample will be stored at −80° C. until being subjected to analysis. Prior to analysis the samples will be warmed to room temperature and reconstituted in 50 µl of deionized LC/MS grade water (LC/MS-ddH$_2$O) and transferred into glass autoinjector vials that then will be loaded onto the Micro AS (Thermo Electron) autoinjector. Twenty µl of each sample will be injected onto a 50×2.1 mm Hypercarb™ Column (Thermo Electron Corporation) on a Surveyor Plus HPLC System (Thermo Electron Corp.) coupled to a LCQ DECA XP Ion Trap Mass Spectrometer (Thermo Electron Corp.) via an ESI (Electro Spray Ionization) source. Chromatographic separation will be achieved by running a gradient from 20 mM perfluoropentanoic acid in LC/MS-ddH$_2$O to 15% acetonitrile in LC/MS-ddH$_2$O in 10 min, then to 26% acetonitrile in LC/MS-ddH$_2$O in an additional 10 min and then to a final 50% acetonitrile in LC/MS-ddH$_2$O over 10 min. Conditions will be held at the final 50% acetonitrile and 20 mM perfluoropentanoic acid in LC/MS-ddH$_2$O for 10 min followed by a return to 100% 20 mM perfluoropentanoic acid in LC/MS-ddH$_2$O for 5 min prior to the next injection.

Figure 16:
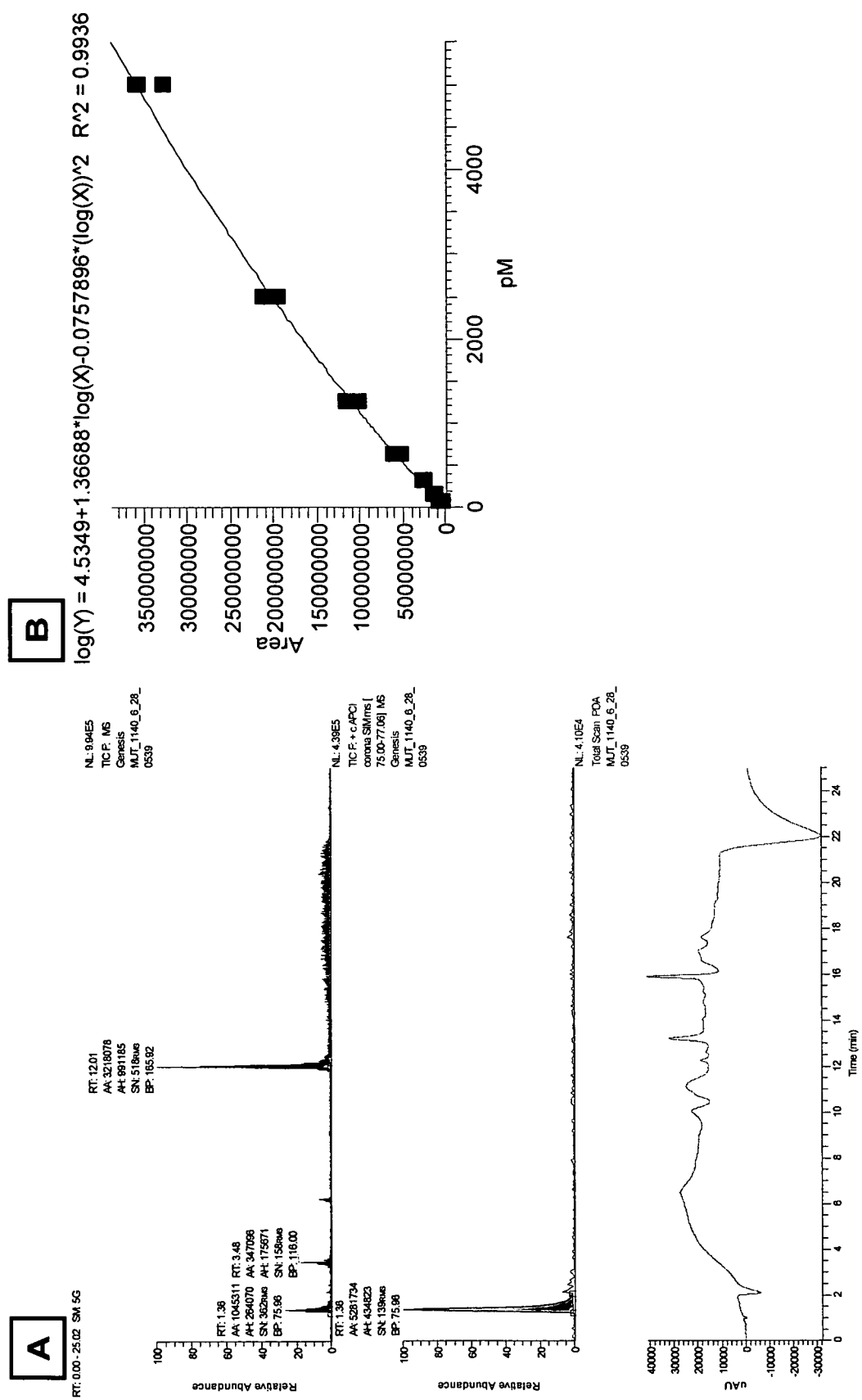

FIG. 16 shows a representative chromatogram and standard curve for use in the quantification of glycine. The data was obtained using a known standard that contained the 24 common amino acids loaded on the column and Selective Ion Monitoring (SIM) for glycine, proline, phenylalanine, lysine and leucine. The results clearly indicate that the assay has the requisite sensitivity for its intended purpose in the proposed research. The assay can be further refined and validated with $C_{13}$-Glycine.

Example 9

Single-Dose Pharmacokinetic Profile and Oral Bioavailability for High Dose Glycine The following experimental design can be used to determine the pharmacokinetic profile and oral bioavailability of glycine. Adult (180 day-old) Sprague-Dawley rats with surgically implanted jugular vein catheters and weighing between 200-225 g from Charles River Laboratories can be used. Eighteen rats will be randomly divided in 3 groups of 6 rats (3 male 3 female) and will be assigned at random to each of three dosage groups: High (5 mg/kg), Medium (2.5 mg/kg), and Low (0.25 mg/kg). Preliminary analysis of plasma samples obtained at necropsy after a 24 hr fast from male ZDF rats fed a diet consisting of 20% glycine by weight indicated a 16.9 µg/mL level of glycine. The actual steady state level of glycine was probably appreciably higher prior to the animals being fasted. Our chosen doses should result in peak plasma levels of ~150 µg/ml, High Dose Group, 75 µg/ml, Medium Dose Group and 7.5 µg/ml Low Dose Group. Glycine will be dissolved in phosphate buffered saline (PBS), pH 7.2 and will be administered first via IV bolus. Plasma samples (0.1 ml) will be drawn into light blue top vacutainer tubes containing citrate (BD #363080) at the following time points T=0 min, T=0.5 min, T=1 min, T=5 min, T=15 min, T=30 min, T=1 hr, T=2 hr, T=4 hr, T=8 hr, T=6 hr T=24 hr and T=4 hr. The separated plasma collected at each time point will be flash frozen in liquid nitrogen and stored at −80° C. until analyzed. Animals will be allowed to recover for a period of seven days, reweighed and then treated with High, Medium and Low Dosages of glycine by oral gavage. Plasma samples, 0.1 ml, will be drawn as previously described for the IV bolus administration into a light blue topped vacutainer at the following time points. T=0 min, T=30 min, T=1 hr, T=2 hr T=4 hr, T=6 hr, T=8 hr, T=16 hr T=24 hr, T=48 hr, T=72 hr and T=96 hr. The separated plasma collected at each time point will be flash frozen in liquid nitrogen and stored at −80° C. until analyzed. Data will be analyzed using WinNonlin® version 4.1 software for Pharmacokinetic analysis. The pharmacokinetic model resulting from these experiments will be used to design the multiple dosing regimens to be used in subsequent experiments. Additionally, this model will serve as a base model for use in selecting analogs for further development.

Example 10

Multiple-Dose Pharmacokinetics of Glycine

In our preliminary studies, glycine was administered orally as part of the normal diet of the test animals. This method of administration did not provide accuracy and reproducibility of dosing necessary for construction of a pharmacodynamic model of glycine's action with respect to induction of apoptosis in adipose tissue. In order to undertake this work we must develop a dosing regimen that will allow us to accurately reflect the observed pharmacologic effect (i.e. induction of apoptosis in adipose tissue). The pharmacokinetic parameters obtained in our studies to define the single dose pharmacokinetic profile and oral bioavailability of high dose glycine will be used to design multiple dosing regimens for high dose glycine. The regimen that is developed will be used to maintain glycine at levels in the blood of test animals at levels equal to ±10% of those observed in animals that were fed a diet consisting of 20%, 10% and 5% glycine by weight in their diet. A detailed description of the number of animals in each dosage group and timing of samples will be determined based on the pharmacokinetic parameters and the variability of parameters ascertained from the previous single-dose studies. We, however, anticipate that the study design would require less than 10 animals (5 male, 5 female) per dosage group in order to validate the regimen. We will use the simulation function of WinNonlin® in the design of the dosing regimen and to develop the time points at which to sample in order to obtain the data to be used to validate the regimen.

WinNonlin® software provides an excellent set of tools for utilizing simulation in the design of multiple dosing schedules and sampling schemes to validate the dosing schedule. GraphPad StatMate version 2.00 for Windows will be used to confirm that the number of animals in each dosage group is that required to achieve proper power in order to demonstrate statistical validity. Statistical analysis will be performed using GraphPad InStat version 3.06 32 bit for Windows. The dosing regimen will be considered to be valid if the PK parameters and circulating levels of glycine in the blood are demonstrated not to differ in a statistically significant manner from those obtained experimentally.

Study animals will be euthanized and necropsies performed at the end of study. The phosphorylation state of BAD at ser-136 in the adipose tissue will be determined either by immunoprecipitation and western blot analysis with anti-BAD ser-136 antibody or by affinity capture LC/MS analysis. See, Papac & Shahrokh, *Mass spectrometry innovations in drug discovery and development*. Pharm Res, 2001. 18(2):131-45; Creaser et al., *Immunoaffinity chromatography combined on-line with high-performance liquid chromatography-mass spectrometry for the determination of corticosteroids*. J Chromatogr A, 1998. 794(1-2): 37-43; Gallo et al., *Development of a liquid chromatography/electrospray tandem mass spectrometry method for confirmation of chloramphenicol residues in milk after alfa-1-acid glycoprotein affinity chromatography*. Rapid Commun Mass Spectrom, 2005. 19(4):574-9. The adipose tissue will also be subjected to immunohistochemical staining for the TUNEL protein as a marker of active apoptosis. See, Pavlovsky & Vagunda, [*Apoptosis-selected methods of detection of apoptosis and associated regulatory factors on tissue sections of tumors*]. Cesk Patol, 2003. 39(1): p. 6-10; Heatwole, V. M., *TUNEL assay for apoptotic cells*. Methods Mol Biol, 1999. 115:141-8; Stadelmann & Lassmann, *Detection of apoptosis in tissue sections*. Cell Tissue Res, 2000. 301(1):19-31.

Major organs will also be harvested and observed for any overt signs of toxicity and preserved for further analysis if any overt signs of toxicity are found.

Example 11

A Linked PK/PD (Pharmacokinetic/Pharmacodynamic Model) for Glycine in Regard to its Ability to Induce Weight Loss Through the Induction of Apoptosis in Adipose Tissue Pharmacodynamics refers to the relationship between drug concentration at the site of action and the pharmacologic response, including biochemical and physiologic effects that interaction. See, Shargel & Yu, *Applied Biopharmaceutics and Pharmacokinetics*. 4th ed. 1999, New York: McGraw-Hill. 573-605.

The form of the pharmacodynamic model is dependent on the mechanism by which the drug asserts its pharmacologic action. Thus, the information obtained in this model will provide useful information in regard to how glycine elicits its biologic effect in adipose tissue. In our preliminary studies for the research proposed in this current grant application we demonstrated that a high glycine diet resulted in BAD at ser-136 being in a dephosphorylated state. We propose to use the phosphorylation state of BAD at ser-136 as a marker of apoptosis for our pharmacodynamic modeling. We will build a PK/PD Link model for glycine action with respect to its effect on the phosphorylation state of BAD. A PK/PD Link model assumes fixed pharmacokinetic parameters in order to model the local concentration of drug at the site of action to be used by the PD model. Jusko, *Corticosteroid pharmacodynamics: models for a broad array of receptor-mediated pharmacologic effects*. J Clin Pharmacol, 1990. 30(4):303-10; Dayneka et al., *Comparison of four basic models of indirect pharmacodynamic responses*. J Pharmacokinet Biopharm, 1993. 21(4):457-78. We will use the pharmacokinetic model derived from the single-dose and multiple dose studies to supply the fixed PK parameters for the PK/PD Linked model. Ex-vivo organ culture of white adipose tissue (WAT) will be used to model the PD portion of the PK/PD Linked model. The methods and procedures for establishing ex-vivo cultures of WAT are well described. See, Moustaid-Moussa & Fried, *Culture of Adipose Tissue and Isolated Adipocytes*, in *Adipose Tissue Protocols*, G. Ailhaud, Editor. 2001, Humana Press, Inc.: Totowa, N.J. p. 197-213; Livingston et al., *Insulin-dependent regulation of the insulin-sensitivity of adipocytes*. Nature, 1978. 273(5661):394-61; Bernstein, *Improved insulin responsiveness in rat adipose tissue pieces cultured with charcoal-treated albumin and oxygen*. J Lipid Res, 1982. 23(2):360-3; Bernstein, *Insulin insensitivity and altered glucose utilization in cultured rat adipose tissue*. J Lipid Res, 1979. 20(7):848-56; Maloff et al., *Direct effects of growth hormone on insulin action in rat adipose tissue maintained in vitro*. Endocrinology, 1980. 107(2):538-44. WAT organ cultures will be used in these experiments, as opposed to isolated adipocytes, because organ cultures more fully reflect the complex biology of WAT resulting in a PD model of concentration versus effect that is more reflective of the in vivo state. Papac & Shahrokh, *Mass spectrometry innovations in drug discovery and development*. Pharm Res, 2001. 18(2):131-45.

In brief, WAT will be obtained within 10 minutes of euthanasia by surgical excision of the retroperitoneal, inguinal, and gonadal fat pads from each of 3 male and 3 female Sprague-Dawley rats weighing 200-225 g. Approximately 12-15 gm of WAT will be obtained from each animal. The WAT from animals of the same sex will be combined and coarsely minced in conical plastic centrifuge tubes (3 g per tube) containing sterile, room temperature M199 (Gibco-BRL; liquid, bicarbonate buffered, supplemented with glutamine and 25 mM HEPES) and 50 µg/mL gentamicin. All further processing of the material will be performed in an aseptic fashion in a laminar flow hood as described by Fried and Moustaid-Moussa (*Culture of Adipose Tissue and Isolated Adipocytes*, in *Adipose Tissue Protocols*, G. Ailhaud, Editor. 2001, Humana Press, Inc.: Totowa, N.J. p. 197-213). The AT will be further minced into 5-10 mg fragments using sharp scissors. Once the tissue is finely minced it can remain at RT for up to 1 h (while the other tubes of tissue are being minced). The tissue will not be placed at 37° C., to avoid increasing its metabolic rate at this juncture. The WAT organ cultures will then be washed free of lipid droplets and blood by pouring the contents of each of the tubes through a nylon mesh (affixed to a funnel), which will be placed on top of a ~500 mL bottle. This will be followed with a wash of at least 300 mL sterile Phosphate Buffered Saline (PBS), at 37° C., over the tissue on the funnel. The washed tissue will then be placed in a sterile tared Petri dish and any large blood clots removed with forceps. The tared Petri dish containing the WAT organ culture will be closed in order to maintain sterility, and then weighed. The WAT will then be placed equally (~0.5 g wet weight/well) into 6 well tissue culture plates using forceps or a perforated spoon. Fresh M199 (Gibco-BRL; liquid, bicarbonate buffered, supplemented with glutamine and 25 mM HEPES) and 50 µg/mL gentamicin will then be immediately added and the cultures maintained in a humidified, 37° C. incubator under an atmosphere of 5% CO2-95% air for 48 hours in order to insure the absence of contamination and sterility.

Triplicate wells containing WAT organ cultures derived from male and female Sprague-Dawley rats prepared as described above will be washed 3× with fresh M199 (Gibco-BRL; liquid, bicarbonate buffered, supplemented with glutamine and 25 mM HEPES), and 50 µg/mL gentamicin The experiment will be initiated by the addition of fresh M199 medium supplemented with the following concentration of glycine. Control wells will receive fresh medium with no additional glycine added, experimental wells will receive M199 medium supplemented with glycine at five equally spaced concentrations with the highest concentration equal to twice the circulating level of glycine in the blood of the highest dose group of the multiple dose PK study. The media will be replenished on a daily basis for a period of 3 days. The cultures will then be harvested and washed 5 times with ice cold PBS. Samples will be prepared for quantification of glycine by the LC/MS method as previously described.

Example 12

Rapid Biochemical Assay for Screening for Bioactive Analogs of Glycine

Dietary glycine at high levels (20% by weight) results in significant weight loss. This weight loss may be a result of the ability of glycine to induce apoptosis in WAT. This is based on preliminary data demonstrating that protein extracts obtained from WAT of treated animals did not have the ability to phosphorylate BAD at serine position 136 (FIGS. 11, 12, and 13). See, Masters et al., *14-3-3 inhibits Bad-induced cell death through interaction with serine*-136. Mol Pharmacol, 2001. 60(6):1325-31; Thompson & Thompson, *Putting the rap on akt*. J Clin Oncol, 2004. 22(20): 4217-26.

As stated previously, others have incidentally observed that glycine is capable of inducing weight loss. However the mechanism by which this occurs has remained unexplained. We believe that glycine has a direct biochemical effect on WAT via regulation of the phosphorylation state of BAD leading to the induction of apoptosis. This is based on the observations in our preliminary experiments that no such dephosphorylation of BAD at ser-136 was observed in BAT or no significant loss of BAT tissue occurred. In addition, we observed that high concentrations of glycine in the medium of 3T3-L1 cells differentiated into adipocytes demonstrated increased staining for TUNEL when compared to non-treated cells. See, Heatwole, *TUNEL assay for apoptotic cells*. Methods Mol Biol, 1999. 115:141-8. An aim of this example is to develop a rapid bioassay that can be used to screen for bioactive analogs of glycine.

We have found that female Sprague-Dawley rats are particularly sensitive to the effects of high glycine in the diet, experiencing rapid significant weight loss. Thus, it would be possible to use significant weight loss in female Sprague-Dawley rats to screen for activity of analogs of glycine. However, this assay is time consuming, would require large-scale synthesis of analogs and would not be efficient for screening large numbers of compounds. We propose to develop a rapid biological in vitro test using differentiated 3T3-L1 cell lines and measurements of the phosphorylation state of BAD at ser-136. Gaillard et al., *Growth of preadipocyte cell lines and cell strains from rodents in serum-free hormone-supplemented medium*. In Vitro, 1984. 20(2):79-88.

In order for such an assay to be used with confidence we must demonstrate that adipocytes from differentiated 3T3-L1 cells respond to high glycine levels in a manner similar to adipocytes in vitro. The following experiments are aimed at demonstrating the utility and validity of using dephosphorylation of BAD at Ser 136 in differentiated 3T3-L1 cells for this purpose.

Adipocytes from WAT will be obtained by modification of the purification process described above for organ culture of WAT. In brief, the WAT will be isolated as previously described and subjected to the following additional steps to obtain isolated adipocyte and stromal-vascular fractions. Isolated adipocyte and stromal fractions will be obtained by subjecting the minced WAT to digestion with Type I Collagenase at a concentration of 1 mg/ml in M199 media at 37° C. for 60 min. The collagenase-treated tissue will then be filtered through a sterile nylon filter (350 µm mesh) into a sterile centrifuge tube. This suspension will be centrifuged at 500× g for 1 min resulting in the separation of the stromal-vascular fraction (pellet) from the adipocyte containing fraction. The respective cell fractions will be washed three additional times in Hank's Balanced Salt Solution. The respective adipocyte and stromal-vascular fractions will then be counted, diluted with fresh M199 media and plated into the wells of six-well culture plates. The cells will be incubated overnight in a 37° C. incubator under an atmosphere of 5% $CO_2$-95% air. The cells will be observed to insure viability and lack of contamination and the experiment will be initiated by the addition of fresh M199 media supplemented with the following increasing concentrations of glycine in the media. Control wells will receive fresh media with no additional glycine added, experimental wells will receive M199 media supplemented with glycine at the same concentrations of glycine used for the PD experiments. The media will be replenished on a daily basis for a period of 3 days. The cultures will then be harvested and washed 5 times with ice cold PBS. The cells will be lysed by exposure to a hypotonic buffer, clarified by centrifugation and aliquots of lysate instantly frozen in liquid nitrogen for storage at −80° C. until use. The intracellular glycine content of the samples will be determined by the LC/MS method. The phosphorylation state of BAD at Ser-136 will be determined either using an ELISA for BAD-Ser 136 or by affinity capture LC/MS analysis. Triplicate wells of each sample condition will be plated and immunohistochemical staining for TUNEL will be performed to demonstrate active apoptosis. We believe the following experiments will provide conclusive evidence that glycine acts directly on adipocytes derived from WAT.

Example 13

Glycine Acts on Adipocytes Derived from Differentiated 3T3-L1 Cells to Induce the Dephosphorylation of BAD and Apoptosis 3T3-L1 cells will be grown in culture and differentiated into adipocytes by standard methodology. See, Négrel & Dani, *Cultures of Adipose Precursor Cells and Cells of Clonal Lines from Animal White Adipose Tissue*, in *Adipose Tissue Protocols*, G. Ailhaud, Editor. 2001, Humana Press, Inc.: Totowa, N.J. p. 225-227. Prior to initiation of the experiment the 3T3-L1 adipocytes will be trypsinized and washed 5 times in dDMEM [containing 1 g/L glucose and 110 mg/L Na pyruvate, supplemented with 3.7 g/L Na bicarbonate, 33 µM biotin, 17 µM pantothenate, antibiotics (62 mg/L penicillin and 50 mg/L streptomycin or 10 mg/L tetracycline), 17 nM insulin and 2 nM T3 and 10% FBS]. Cells will be plated into the wells of six well culture plates at a density of $8.5 \times 10^3$ cells/cm². The cells will be observed to insure viability and lack of contamination and the experiment will be initiated by the addition of fresh dDMEM media supplemented with the following increasing concentrations of glycine in the media. Control wells will receive fresh media with no additional glycine added, experimental wells will receive dDMEM media supplemented with glycine at the same concentrations of glycine as used for the PD experiments. The media will be replenished on a daily basis for a period of 3 days. The cultures will then be harvested and washed 5 times with ice cold PBS. The cells will be lysed by exposure to a hypotonic buffer, clarified by centrifugation and aliquots of lysate instantly frozen in liquid nitrogen for storage at −80° C. until use. The intracellular glycine content of the samples will be determined by the LC/MS method. The phosphorylation state of BAD at Ser-136 will be determined either using an ELISA for BAD-Ser 136 or by affinity capture LC/MS analysis. Preliminary experiments indicate that glycine at concentrations in the media equivalent to 2× the normal circulating levels in the blood cause 3T3-L1 adipocytes to undergo apoptosis as evidenced by positive TUNEL staining. Triplicate wells of each sample condition will be plated and immunohistochemical staining for TUNEL will be performed to demonstrate active apoptosis.

Example 14

2D-Gel and ICAT (Isotope Coded Affinity Tag) Analysis to Confirm that Glycine Treatment is Eliciting Equivalent Biological Response in Adipocytes Derived from WAT and Differentiated 3T3-L1 Cells The utility of adipocytes derived from differentiation of 3T3-L1 cells will be further verified by demonstrating that the patterns of differentially expressed proteins elicited with glycine treatment is similar to the pattern seen in glycine-treated WAT protein extracts using 2D-gel and ICAT analysis. See, Patton et al., *Two-dimensional gel electrophoresis; better than a poke in the ICAT?* Curr Opin Biotechnol, 2002. 13(4): p. 321-8.

Figure 17:
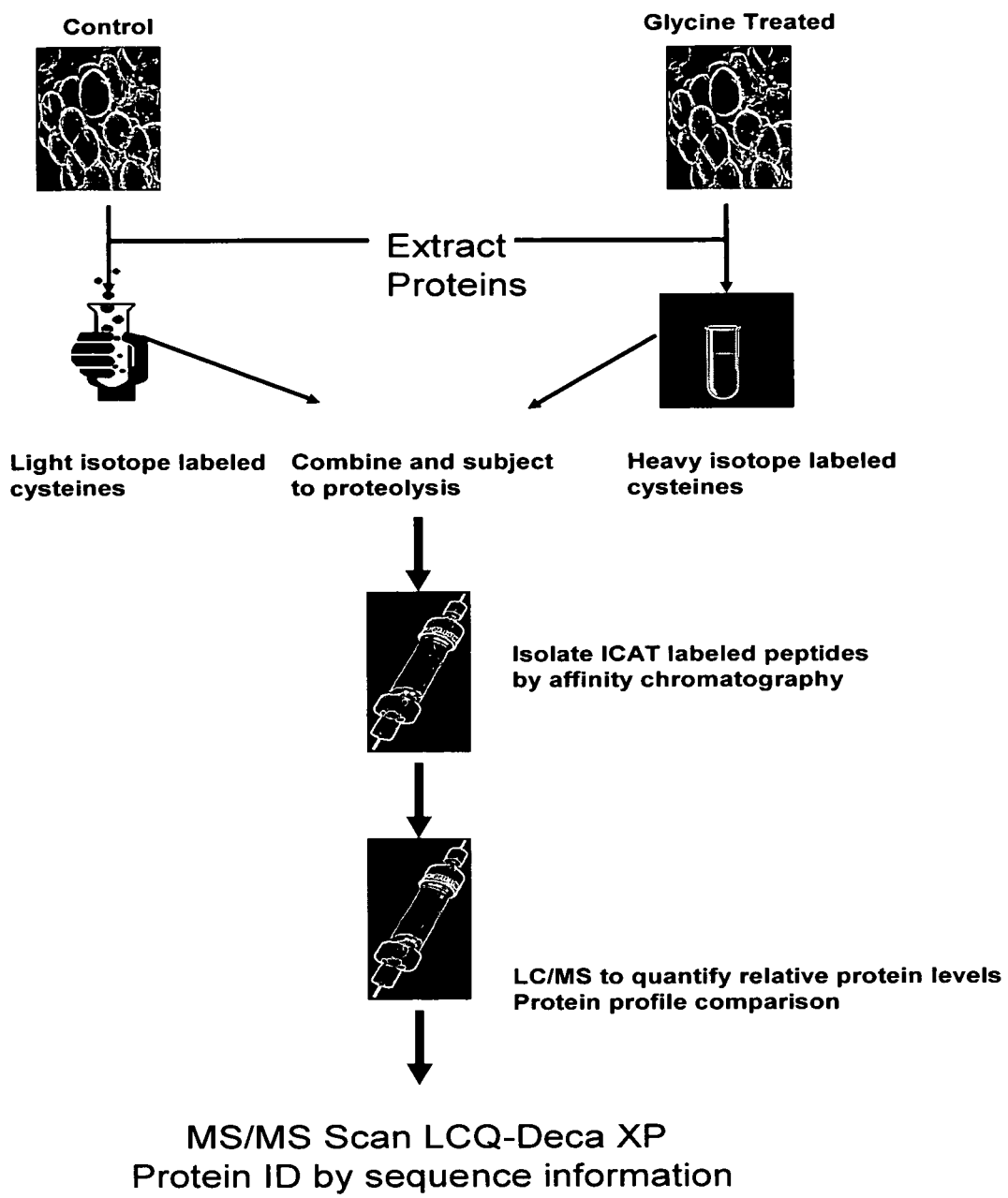
FIG. 17 shows an (Isotope Coded Affinity Tag) process.

In brief, WAT and 3T3-L1 derived adipocytes will be obtained as previously described. Control and concentration of glycine in experimental wells will be treated as described above. Samples for analysis will be prepared as previously described and equal amounts of samples will be subjected to analysis by 2D-Gel and ICAT analysis in order to demonstrate the 3T3-L1 adipocytes and WAT derived adipocytes are responding in a biologically equivalent manner to glycine treatment. Analysis by ICAT can provide a starting point for elucidating the mechanism of action by which glycine induces apoptosis in adipocytes form WAT. ICAT is a powerful method capable of identifying which proteins differ between glycine and treated cells in a quantifiable fashion. The ICAT methodology is presented diagrammatically in FIG. 17.

Example 15

Synthesis of a Library of Structural Analogs of Glycine and Pre-Screen the Compounds for the Ability to Induce Apoptosis 3T3-Adipocytes Glycine is a readily available, non-toxic amino acid. Glycine, glycine analogs, or a combination thereof should induce weight loss through the induction of apoptosis in WAT. The following series of glycine analogs can be synthesized:

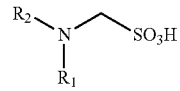

Formula I

R1 = R2 = H; Pr, Bn
R1 = R2 = Me, Et, Pr Me, Et, Pr, Bn
R1 = H, R2 = Bn; R1
R3 = Me, Et, Pr, Bn
R2 = (CH$_2$)$_5$ = Me, Et, Pr, or Bn.

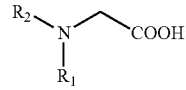

Formula II

R1 = R2 = H
R1 = R2 = Me, Et, Pr
R1 = H, R2 = Bn
R1, R2 = (CH$_2$)$_5$

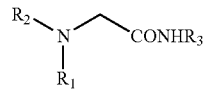

Formula III

R1 = R2 = H, and R3 = H, Me, Et,
R1 = R2 = Me, Et, Pr, and R3 =
R1 = H, R2 = Bn or Me,
R1, R2 = (CH$_2$)$_5$ or Me, R3

The Formula I series can be synthesized, for example, by the following scheme:

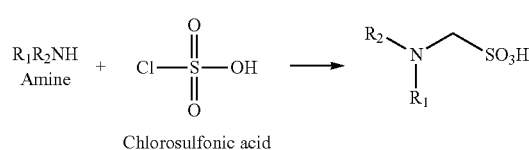

Chlorosulfonic acid

The amino sulfonic acid analogs proposed in the above scheme will be synthesized by treating various dialkyl amines such as dimethyl amine with chloro-methanesulfonic acid. The Formula II series can be synthesized by, for example, by the following scheme:

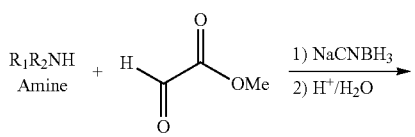

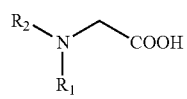

The above shown analogs will be synthesized by treating dialkylamines or primary amines with Oxo-acetic acid methyl ester under reductive conditions using sodium cyanoborohydride as the reducing agent. The products will be purified by chromatography. Formula III can be synthesized by, for example, the following scheme:

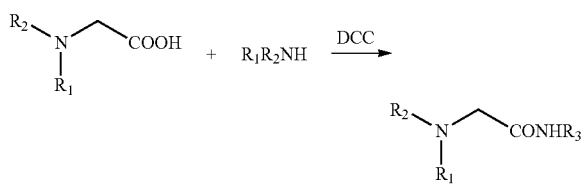

The free carboxy terminus of N(alkyl) or N,N-Dialkyl glycine will be amidated with an amine in the presence of Dicylcohexyl carbodiimide (DCC) and dimethylaminopyridine(DMAP). In all cases the products will be purified by chromatography. The identity, purity and quantity will be ascertained by mass spectrometry, NMR, analytical liquid chromatography and any other analytical methodology as required.

The synthesized analogs will be subjected to a primary screen for their ability to promote the dephosphorylation of BAD at Ser-136. The analog will be screened at the same concentration with a no-glycine supplemented control and positive control of glycine in the media at the same concentration and at a known effective concentration. All assays will be performed in triplicate. All potential positive analogs will be subjected to a repeat screening. Secondary screening of identified positive compounds in in vitro tests to ascertain their chemical properties make them good drug candidates for in vivo testing.

Example 16

Immature Animals

Figure 10:
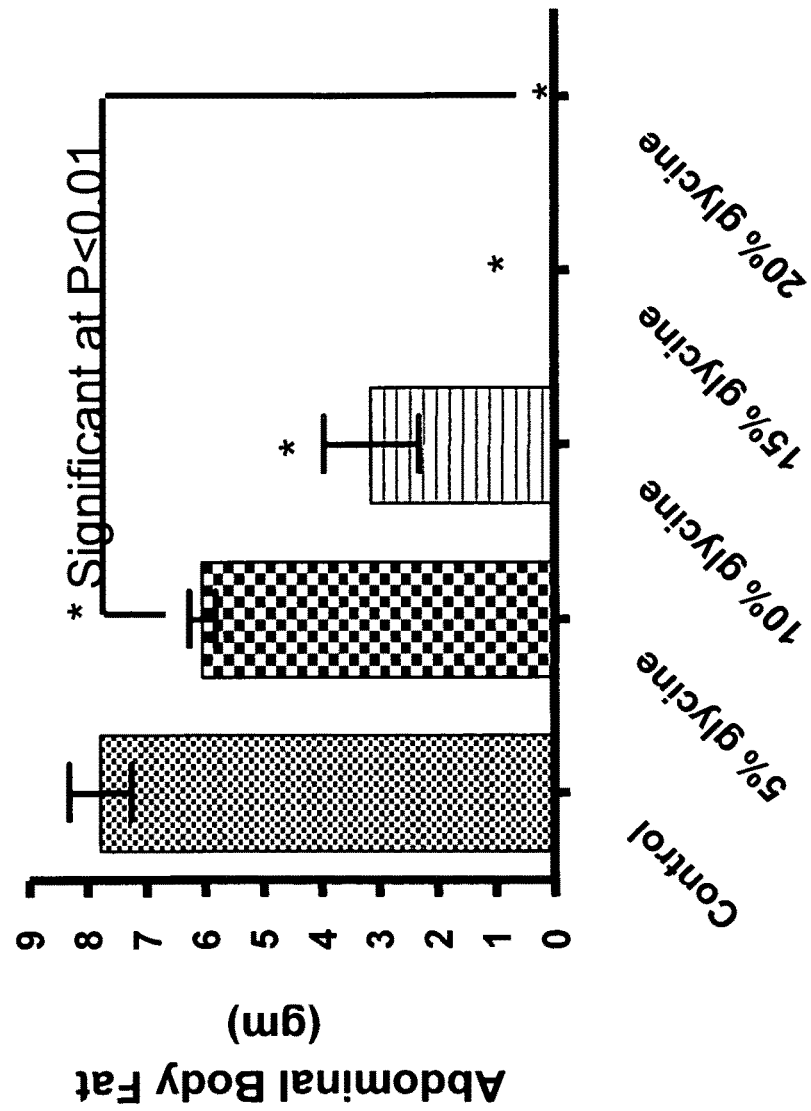
FIG. 10 shows the effect of a 5%, 10%, 15%, and 20% glycine diet, and a non-supplemented diet on the abdominal fat content in female Sprague-Dawley rats.

FIGS. 18 and 19 show that the addition of glycine to the diet of immature female Sprague Dawley rats resulted in a dose-dependent reduction in weight gain and growth, respectively. Animals treated for 4 weeks with diet supplemented with glycine were switched to diet containing no glycine supplementation (FIGS. 18 and 19, 10% to 0%). This resulted in rapid growth and weight gain, such that within one month, they were the same size and weight as the control animals in Group 1. FIGS. 20 and 21 show that the addition of glycine to the diet of immature male Sprague Dawley rats resulted in a dose-dependent reduction in weight gain and growth, respectively. Animals treated for 4 weeks with diet supplemented with glycine were switched to diet containing no glycine supplementation (FIGS. 20 and 21, 10% to 0%). This resulted in rapid growth and weight gain, such that within one month, they were the same size and weight as the control animals in Group 1.

We claim:

1. A method for reducing white adipose tissue in an overweight or obese animal comprising administering a high glycine diet comprising 10% to 30% glycine by weight of the diet to the animal, wherein white adipose tissue in the overweight or obese animal is reduced.

2. A method for inducing apoptosis in white adipocytes of an overweight or obese animal comprising administering a high glycine diet comprising 10% to 30% glycine by weight of the diet to the overweight or obese animal, wherein apoptosis of white adipocytes in the overweight or obese animal is induced.

3. A method for producing weight loss in an overweight or obese animal comprising administering a high glycine diet comprising 10% to 30% glycine by weight of the diet to the overweight or obese animal, wherein weight loss in the overweight or obese animal is produced.

4. The method of claim 3, wherein the method for producing weight loss comprises reducing fat content in the overweight or obese animal.

5. The method of claim 3, wherein the method further comprises an adjunctive weight loss therapy comprising an exercise regimen, surgical intervention, behavioral therapy, pharmacotherapy, or a combination thereof.

6. The method of claim 3, wherein the animal is an adult animal.

7. The method of claim 3, wherein the animal is a human.

8. The method of claim 1, wherein the animal is a mature animal.

9. The method of claim 3, wherein the animal is a mature animal.

10. The method of claim 1, wherein the animal is an adult animal.

11. The method of claim 1, wherein the animal is a human.

12. The method of claim 3, wherein no deleterious side effects are caused by the method.

13. The method of claim 3, wherein the animals a dog.

* * * * *